(12) United States Patent
Price et al.

(10) Patent No.: US 8,998,939 B2
(45) Date of Patent: Apr. 7, 2015

(54) SURGICAL INSTRUMENT WITH MODULAR END EFFECTOR

(75) Inventors: Daniel W. Price, Loveland, OH (US); Richard W. Timm, Cincinnati, OH (US); Kyle P. Moore, Mason, OH (US); Gregory W. Johnson, Cincinnati, OH (US); John B. Schulte, West Chester, OH (US); Daniel J. Mumaw, Johannesburg (ZA); Kevin L. Houser, Springboro, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 13/274,805

(22) Filed: Oct. 17, 2011

(65) Prior Publication Data

US 2012/0116396 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 17/32* (2006.01)
*A61B 18/14* (2006.01)
(Continued)

(52) U.S. Cl.
CPC ....... *A61B 18/1442* (2013.01); *A61B 17/00234* (2013.01); *A61B 17/320068* (2013.01); *A61B 17/320092* (2013.01); *A61B 18/00* (2013.01); *A61B 18/04* (2013.01); *A61B 18/12* (2013.01); *A61B 18/14* (2013.01);
(Continued)

(58) Field of Classification Search
USPC .......................... 606/39, 45, 169–185; 601/2
See application file for complete search history.

(56) References Cited

U.S. PATENT DOCUMENTS

| 1,754,806 A | 4/1930 | Stevenson |
|---|---|---|
| 3,297,192 A | 1/1967 | Swett |

(Continued)

FOREIGN PATENT DOCUMENTS

| DE | 102008051866 | 10/2010 |
|---|---|---|
| DE | 102009013034 | 10/2010 |

(Continued)

OTHER PUBLICATIONS

U.S. Appl. No. 13/151,471, filed Jun. 2, 2011, Stulen.
(Continued)

*Primary Examiner* — Katherine M Shi

(57) ABSTRACT

A surgical instrument may include a reusable body assembly, a reusable transducer and blade assembly, and a disposable end effector. The transducer and blade assembly may be latched into the body assembly. One version may include an electrical connector on the latch member to electrically couple the body assembly to the transducer. The end effector may include an outer sheath portion coupleable to an outer sheath of the body assembly via a bayonet connection and a clamp arm pivotably coupled to the outer sheath portion. In some versions, an inner tubular member of the body assembly may also couple to an inner tube portion via a bayonet connection. The inner tubular member may include a key to align with a slot on the transducer and blade assembly to align the clamp arm with the blade. The end effector may alternatively couple via threading or ratcheting teeth having a slip feature.

20 Claims, 10 Drawing Sheets

(51) Int. Cl.
*A61B 17/00* (2006.01)
*A61B 18/00* (2006.01)
*A61B 18/04* (2006.01)
*A61B 18/12* (2006.01)
*H02J 7/00* (2006.01)
*H01M 2/26* (2006.01)
*H01M 2/10* (2006.01)
*A61B 17/064* (2006.01)
*A61B 17/285* (2006.01)
*A61B 19/00* (2006.01)
*A61B 17/29* (2006.01)

(52) U.S. Cl.
CPC .......... *A61B 18/1445* (2013.01); *H02J 7/0045* (2013.01); *H01M 2/26* (2013.01); *H01M 2/10* (2013.01); *A61B 18/1206* (2013.01); *A61B 17/064* (2013.01); *A61B 17/285* (2013.01); *A61B 18/1233* (2013.01); *A61B 19/38* (2013.01); *A61B 2017/00084* (2013.01); *A61B 2017/00398* (2013.01); *A61B 2017/0046* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/2929* (2013.01); *A61B 2017/293* (2013.01); *A61B 2017/2931* (2013.01); *A61B 2017/2933* (2013.01); *A61B 2017/294* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01)

(56) References Cited

U.S. PATENT DOCUMENTS

| | | | |
|---|---|---|---|
| 3,419,198 | A | 12/1968 | Pettersen |
| 3,619,671 | A | 11/1971 | Shoh |
| 4,034,762 | A | 7/1977 | Cosens et al. |
| 4,057,220 | A | 11/1977 | Kudlacek |
| 4,535,773 | A | 8/1985 | Yoon |
| 4,641,076 | A | 2/1987 | Linden et al. |
| 4,662,068 | A | 5/1987 | Polonsky |
| 4,666,037 | A | 5/1987 | Weissman |
| 4,717,018 | A | 1/1988 | Sacherer et al. |
| 4,717,050 | A | 1/1988 | Wright |
| 4,721,097 | A | 1/1988 | D'Amelio |
| 4,768,969 | A | 9/1988 | Bauer et al. |
| 4,800,878 | A | 1/1989 | Cartmell |
| 4,844,259 | A | 7/1989 | Glowczewskie, Jr. et al. |
| 4,878,493 | A | 11/1989 | Pasternak et al. |
| 5,071,417 | A | 12/1991 | Sinofsky |
| 5,107,155 | A | 4/1992 | Yamaguchi |
| 5,144,771 | A | 9/1992 | Miwa |
| 5,169,733 | A | 12/1992 | Savovic et al. |
| 5,176,677 | A | 1/1993 | Wuchinich |
| 5,246,109 | A | 9/1993 | Markle et al. |
| 5,273,177 | A | 12/1993 | Campbell |
| 5,277,694 | A | 1/1994 | Leysieffer et al. |
| 5,308,358 | A | 5/1994 | Bond et al. |
| 5,322,055 | A | 6/1994 | Davison |
| 5,339,799 | A | 8/1994 | Kami et al. |
| 5,358,508 | A | 10/1994 | Cobb et al. |
| 5,361,902 | A | 11/1994 | Abidin et al. |
| 5,429,229 | A | 7/1995 | Chester et al. |
| 5,449,370 | A | 9/1995 | Vaitekunas |
| 5,454,378 | A | 10/1995 | Palmer et al. |
| 5,501,607 | A | 3/1996 | Yoshioka et al. |
| 5,507,297 | A | 4/1996 | Slater et al. |
| 5,561,881 | A | 10/1996 | Klinger et al. |
| 5,578,052 | A | 11/1996 | Koros et al. |
| 5,580,258 | A | 12/1996 | Wakata |
| 5,582,617 | A * | 12/1996 | Klieman et al. ............... 606/170 |
| 5,590,778 | A | 1/1997 | Dutchik |
| 5,592,065 | A | 1/1997 | Oglesbee et al. |
| 5,597,531 | A | 1/1997 | Liberti et al. |
| 5,599,350 | A | 2/1997 | Schulze et al. |
| 5,630,420 | A | 5/1997 | Vaitekunas |
| 5,630,456 | A | 5/1997 | Hugo et al. |
| 5,690,222 | A | 11/1997 | Peters |
| 5,741,305 | A | 4/1998 | Vincent et al. |
| 5,776,155 | A | 7/1998 | Beaupre et al. |
| 5,800,336 | A | 9/1998 | Ball et al. |
| 5,817,128 | A | 10/1998 | Storz |
| 5,868,244 | A | 2/1999 | Ivanov et al. |
| 5,873,873 | A | 2/1999 | Smith et al. |
| 5,882,310 | A | 3/1999 | Marian, Jr. |
| 5,935,144 | A | 8/1999 | Estabrook |
| 5,938,633 | A | 8/1999 | Beaupre |
| 5,944,737 | A | 8/1999 | Tsonton et al. |
| 5,951,575 | A | 9/1999 | Bolduc et al. |
| 5,980,510 | A | 11/1999 | Tsonton et al. |
| 5,997,531 | A | 12/1999 | Loeb et al. |
| 6,018,227 | A | 1/2000 | Kumar et al. |
| 6,051,010 | A | 4/2000 | Dimatteo et al. |
| 6,056,735 | A | 5/2000 | Okada et al. |
| 6,063,098 | A | 5/2000 | Houser et al. |
| 6,066,151 | A * | 5/2000 | Miyawaki et al. ............. 606/169 |
| 6,083,191 | A | 7/2000 | Rose |
| 6,099,537 | A | 8/2000 | Sugai et al. |
| 6,165,191 | A | 12/2000 | Shibata et al. |
| 6,204,592 | B1 | 3/2001 | Hur |
| 6,214,023 | B1 | 4/2001 | Whipple et al. |
| 6,246,896 | B1 | 6/2001 | Dumoulin et al. |
| 6,248,238 | B1 | 6/2001 | Burtin et al. |
| 6,325,811 | B1 | 12/2001 | Messerly |
| 6,339,368 | B1 | 1/2002 | Leith |
| 6,398,755 | B1 | 6/2002 | Belef et al. |
| 6,409,742 | B1 | 6/2002 | Fulton, III et al. |
| 6,500,176 | B1 | 12/2002 | Truckai et al. |
| 6,500,188 | B2 | 12/2002 | Harper et al. |
| 6,514,267 | B2 | 2/2003 | Jewett |
| 6,520,185 | B1 | 2/2003 | Bommannan et al. |
| 6,561,983 | B2 | 5/2003 | Cronin et al. |
| 6,609,414 | B2 | 8/2003 | Mayer et al. |
| 6,623,500 | B1 | 9/2003 | Cook et al. |
| 6,626,901 | B1 | 9/2003 | Treat et al. |
| 6,647,281 | B2 | 11/2003 | Morency |
| 6,650,975 | B2 | 11/2003 | Ruffner |
| 6,656,177 | B2 | 12/2003 | Truckai et al. |
| 6,658,301 | B2 | 12/2003 | Loeb et al. |
| 6,666,875 | B1 | 12/2003 | Sakurai et al. |
| 6,717,193 | B2 | 4/2004 | Olewine et al. |
| 6,730,042 | B2 | 5/2004 | Fulton et al. |
| 6,758,855 | B2 | 7/2004 | Fulton, III et al. |
| 6,761,698 | B2 | 7/2004 | Shibata et al. |
| 6,783,524 | B2 | 8/2004 | Anderson et al. |
| 6,815,206 | B2 | 11/2004 | Lin et al. |
| 6,821,671 | B2 | 11/2004 | Hinton et al. |
| 6,838,862 | B2 | 1/2005 | Luu |
| 6,860,880 | B2 | 3/2005 | Treat et al. |
| 6,869,435 | B2 | 3/2005 | Blake |
| 6,923,807 | B2 | 8/2005 | Ryan et al. |
| 6,982,696 | B1 | 1/2006 | Shahoian |
| 7,031,155 | B2 | 4/2006 | Sauciuc et al. |
| 7,077,853 | B2 | 7/2006 | Kramer et al. |
| 7,101,371 | B2 | 9/2006 | Dycus et al. |
| 7,112,201 | B2 | 9/2006 | Truckai et al. |
| 7,125,409 | B2 | 10/2006 | Truckai et al. |
| 7,150,712 | B2 | 12/2006 | Buehlmann et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,221,216 | B2 | 5/2007 | Nguyen |
| 7,232,440 | B2 | 6/2007 | Dumbauld et al. |
| 7,244,024 | B2 | 7/2007 | Biscardi |
| 7,292,227 | B2 | 11/2007 | Fukumoto et al. |
| 7,296,804 | B2 * | 11/2007 | Lechot et al. ................. 279/75 |

(56) References Cited

U.S. PATENT DOCUMENTS

| | | |
|---|---|---|
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0114873 A1 * | 6/2003 | Banko et al. ............... 606/169 |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 * | 4/2006 | Houser et al. ............... 606/40 |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240204 A1 * | 9/2009 | Taylor et al. ............... 604/167.03 |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0077514 A1 | 3/2011 | Ulric et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |

(56) References Cited

U.S. PATENT DOCUMENTS

| | | | |
|---|---|---|---|
| 2011/0224668 | A1 | 9/2011 | Johnson et al. |
| 2011/0247952 | A1 | 10/2011 | Hebach et al. |
| 2012/0179036 | A1 | 7/2012 | Patrick et al. |
| 2012/0265230 | A1 | 10/2012 | Laurent et al. |
| 2012/0283732 | A1 | 11/2012 | Lam |
| 2012/0292367 | A1 | 11/2012 | Morgan et al. |
| 2013/0085330 | A1 | 4/2013 | Ramamurthy et al. |
| 2013/0085332 | A1 | 4/2013 | Ramamurthy et al. |
| 2013/0085397 | A1 | 4/2013 | Ramamurthy et al. |
| 2013/0090528 | A1 | 4/2013 | Ramamurthy et al. |
| 2013/0090530 | A1 | 4/2013 | Ramamurthy et al. |
| 2013/0090552 | A1 | 4/2013 | Ramamurthy et al. |
| 2013/0116690 | A1 | 5/2013 | Unger et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prothesis, Transducers'97, vol. 1, International Conference on Solid State Sensors and Actuators, (Jun. 16-19, 1997) pp. 433-433 (Abstract).
"System 6 Aseptic Battery System," Stryker (2006) pp. 1-2.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011 /059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
International Search Report dated Jan. 26, 2012 for Application No. PCT/US11/059220.

(56) References Cited

OTHER PUBLICATIONS

International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
International Search Report and Written Opinion dated Jul. 6, 2012 for PCT/US2011/059381.
Office Action Non-Final dated Aug. 6, 2013 for U.S. Appl. No. 13/151,471.
Notice of Allowance dated Dec. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Restriction Requirement dated Dec. 9, 2013 for U.S. Appl. No. 13/274,496.
Office Action Final dated Aug. 16, 2013 for U.S. Appl. No. 13/274,516.
Office Action Non-Final dated Dec. 6, 2013 for U.S. Appl. No. 13/274,516.
Office Action Final dated Oct. 25, 2013 for U.S. Appl. No. 13/274,540.
Office Action Non-Final dated Jun. 14, 2013 for U.S. Appl. No. 13/274,830.
Office Action Final dated Nov. 26, 2013 for U.S. Appl. No. 13/274,830.
Office Action Final dated Dec. 5, 2013 for U.S. Appl. No. 13/275,495.
Office Action Non-Final dated Jan. 6, 2014 for U.S. Appl. No. 13/275,514.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.

(56) References Cited

OTHER PUBLICATIONS

International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9. 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.

\* cited by examiner

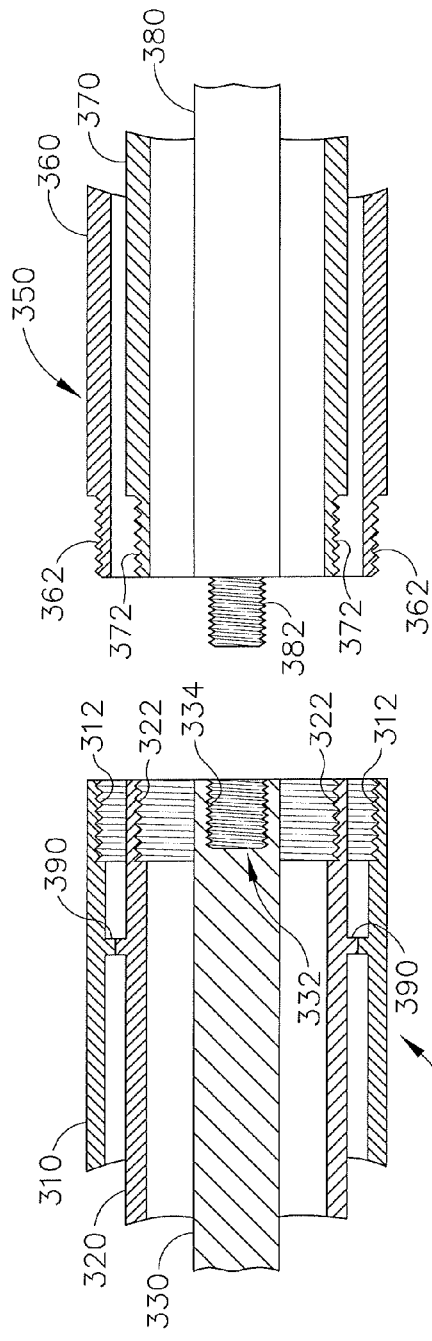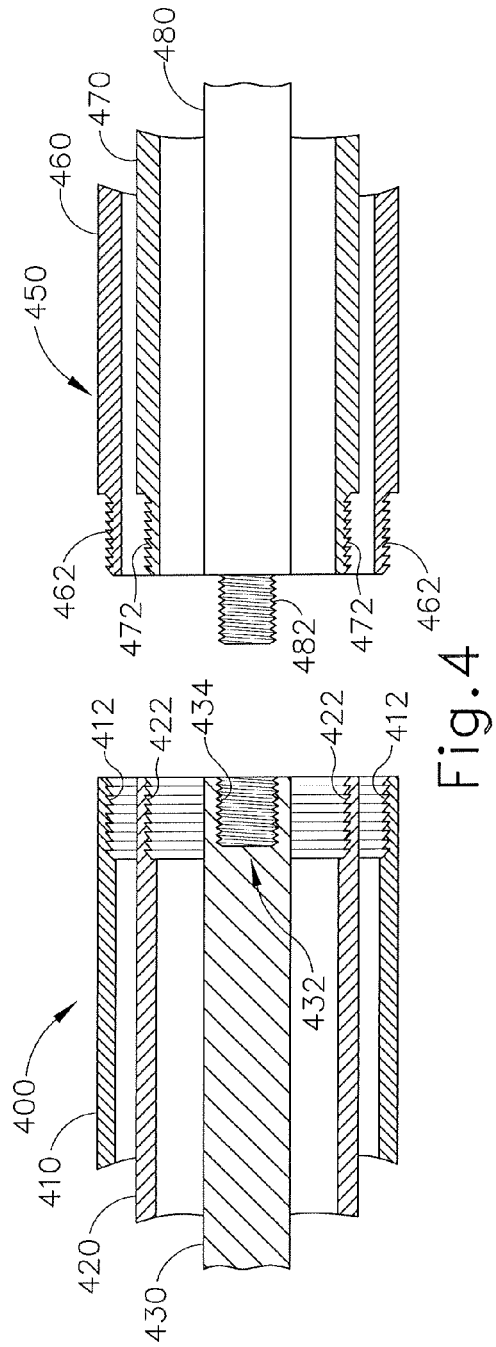

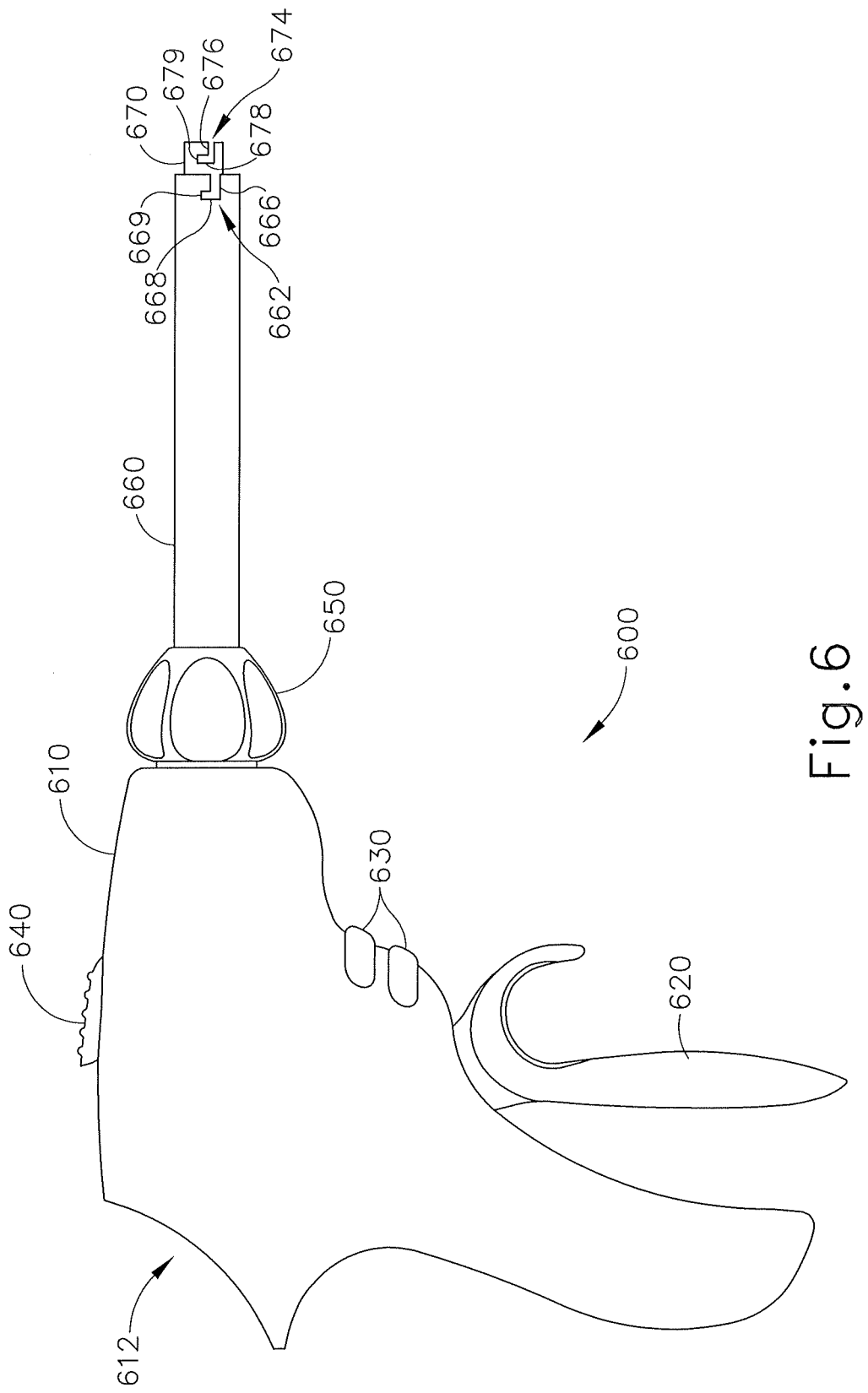

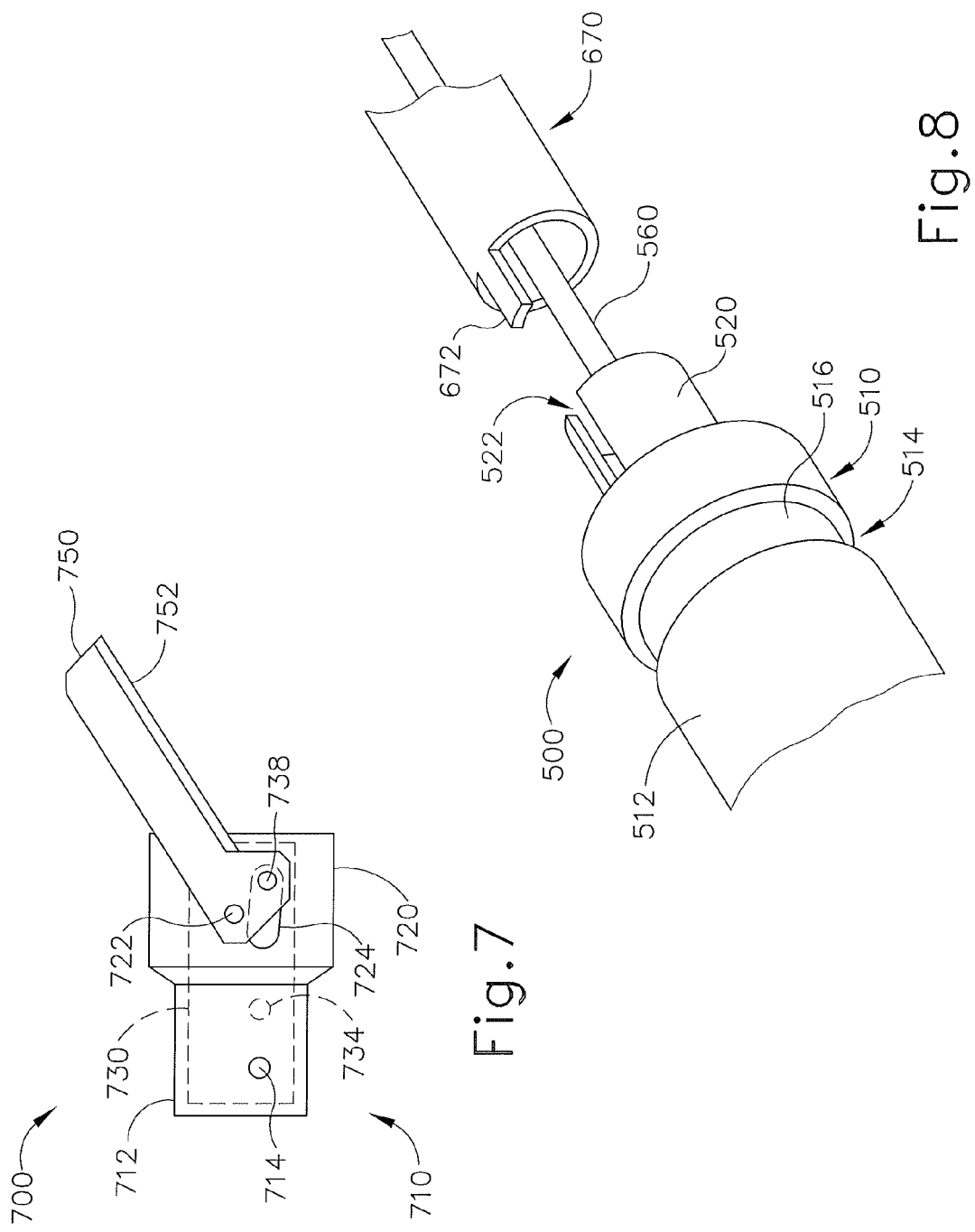

SURGICAL INSTRUMENT WITH MODULAR END EFFECTOR

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, issued Jun. 11, 2013 as U.S. Pat. No 8,461,744, entitled "Rotating Transducer Mount for Ultrasonic Surgical Instruments," published Jan. 20, 2011, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, the disclosure of which is incorporated by reference herein. Additionally, such surgical tools may include a cordless transducer such as that disclosed in U.S. Pat. Pub. No. 2009/0143797, issued Apr. 16, 2013 as U.S. Pat. No. 8,419,757, entitled "Cordless Hand-held Ultrasonic Cautery Cutting Device," published Jun. 4, 2009, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a partial side cross-sectional view of an exemplary threaded end effector;

FIG. 4 depicts a partial side cross-sectional view of an exemplary ratcheting end effector;

FIG. 6 depicts a side elevation view of an exemplary handle assembly showing an outer sheath and an inner tubular actuation member each having a bayonet slot;

FIG. 7 depicts a side elevation view of an exemplary detachable end effector showing bayonet pins on an outer sheath portion and an inner tube portion;

FIG. 8 depicts a partial perspective view of a portion of the transducer and blade assembly of FIG. 5 and a proximal end of the inner tubular actuation member of the handle assembly of FIG. 6 showing a key and slot;

Figure 1:
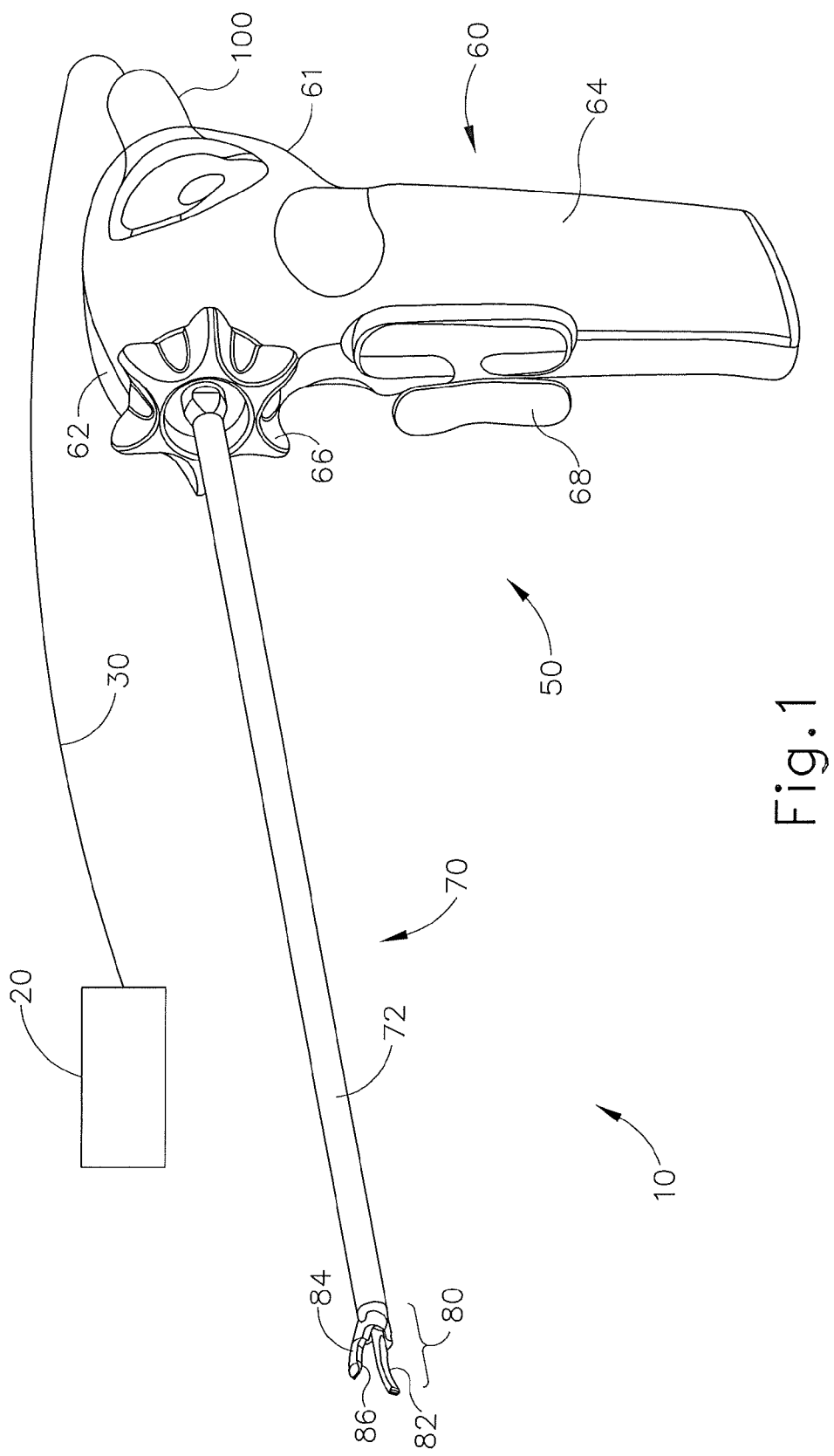
FIG. 1 depicts a perspective view of an exemplary surgical system having a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. In addition or in the alternative, generator (20) may be constructed in accordance with at least some of the teachings of in U.S. Pat. Pub. No. 2011/0087212, entitled "Surgical Generator for Ultrasonic and Electrosurgical Devices," published Apr. 14, 2011, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, issued Apr. 16, 2013 as U.S. Pat. No. 8,419,757, entitled "Cordless Hand-held Ultrasonic Cautery Cutting Device," published Jun. 4, 2009, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is herein incorporated by reference.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuation member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the distal end of transmission assembly (70), and a clamp pad (86) coupled to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

In some versions, transducer (100) comprises a plurality of piezoelectric elements (not shown) that are compressed between a first resonator (not shown) and a second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example. Transducer (100) further comprises electrodes, including at least one positive electrode and at least one negative electrode, that are configured to create a voltage potential across the one or more piezoelectric elements, such that the piezoelectric elements convert the electrical power into ultrasonic vibrations. When transducer (100) of the present example is activated, transducer (100) is operable to create linear oscillations or vibrations at an ultrasonic frequency (such as 55.5 kHz). When transducer (100) is coupled to transmission assembly (70), these linear oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever tissue and denature the proteins in adjacent tissue cells, thereby providing a coagulative effect with relatively little thermal spread. An electrical current may also be provided through blade (82) and clamp arm (84) to cauterize the tissue. One merely exemplary suitable ultrasonic transducer (100) is Model No. HP054, sold by Ethicon Endo-Surgery, Inc. of Cincinnati, Ohio, though it should be understood that any other suitable transducer may be used. Transducer (100) may further be constructed in accordance with at least some of the teachings of U.S. patent application Ser. No. 13/269,883 entitled "Surgical Instrument with Clutching Slip Ring Assembly to Power Ultrasonic Transducer," filed Oct. 10, 2011; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660 (now U.S. Pat. No. 8,461,744); U.S. Pat. No. 6,500,176; U.S. Pat. Pub. No. 2011/0087218; and/or U.S. Pat. Pub. No. 2009/0143797, the disclosures of which are herein incorporated by reference.

Multi-piece handle assembly (60) of the present example comprises a mating housing portion (62) and a lower portion (64). Mating housing portion (62) defines a cavity within multi-piece handle assembly (60) and is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011 (now U.S. Pat. No. 8,461,744), the disclosure of which is incorporated by reference herein.

In some versions toggle buttons are located on a distal surface of lower portion (64) and are operable to selectively activate transducer (100) at different operational levels using generator (20). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, only a single toggle button may be provided or more than two toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic casing (61) (such as polycarbonate or a liquid crystal polymer), ceramics, metals and/or any other suitable material as will be apparent to one of ordinary skill in the art in view of the teachings herein. Other configurations for multi-piece handle assembly (60) will also be apparent to those of ordinary skill in the art in view of the teachings herein. For instance, in some versions trigger (68) may be omitted and surgical instrument (50) may be activated by a controlled of a robotic system. In other versions, surgical instrument (50) may be activated when coupled to generator (20).

Further still, surgical instrument (50) may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, issued Apr. 16, 2013 as U.S. Pat. No. 8,419,757, the disclosure of which is incorporated by reference herein; U.S. Pub. No. 2010/0069940 entitled "Ultrasonic Device for Fingertip Control," published Mar. 18, 2010, the disclosure of which is incorporated by reference herein; U.S. Pub. No. 2011/0015660, entitled "Rotating Transducer Mount for Ultrasonic Surgical Instruments," published Jan. 20, 2011, issued Jun. 11, 2013 as U.S. Pat. No. 8,461,744, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Modular End Effector Assemblies

In some situations, it may be preferable to detach only clamp arm (84), a portion of an inner tubular actuation member, a portion of outer sheath (72), and/or blade (82) from surgical instrument (50). For instance, portions of outer sheath (72), portions of inner tubular actuation member, blade (82), and/or clamp arm (84) may be rendered unclean during a surgical procedure. In such instances, it may be difficult to clean and resterilize the portion of outer sheath (72), portion of inner tubular actuation member, blade (82), and/or clamp arm (84) between uses due to the pivotable connection of clamp arm (84) to the inner tubular actuation member and outer sheath (72). Accordingly, it may be preferable to have a disposable end effector that may be coupled and decoupled from the rest of surgical instrument (50). The remainder of surgical instrument (50) may be configured to be reusable, reclaimable, and/or resterilizable. Thus, a user may discard a used end effector, resterilize the remainder of surgical instrument (50), and couple a new end effector onto surgical instrument (50) for use in another procedure. In other situations, it may be useful to be able to change end effectors if clamp arm (84) and/or clamp pads (86) wear out, jam, and/or are rendered inoperable or unusable. In such situations, it may be useful to be able to change end effectors rather than transmission assemblies (70) and/or surgical instruments (50). Accordingly, various configurations for decoupleable end effectors will be described below.

A. Exemplary End Effector

Figure 2A:
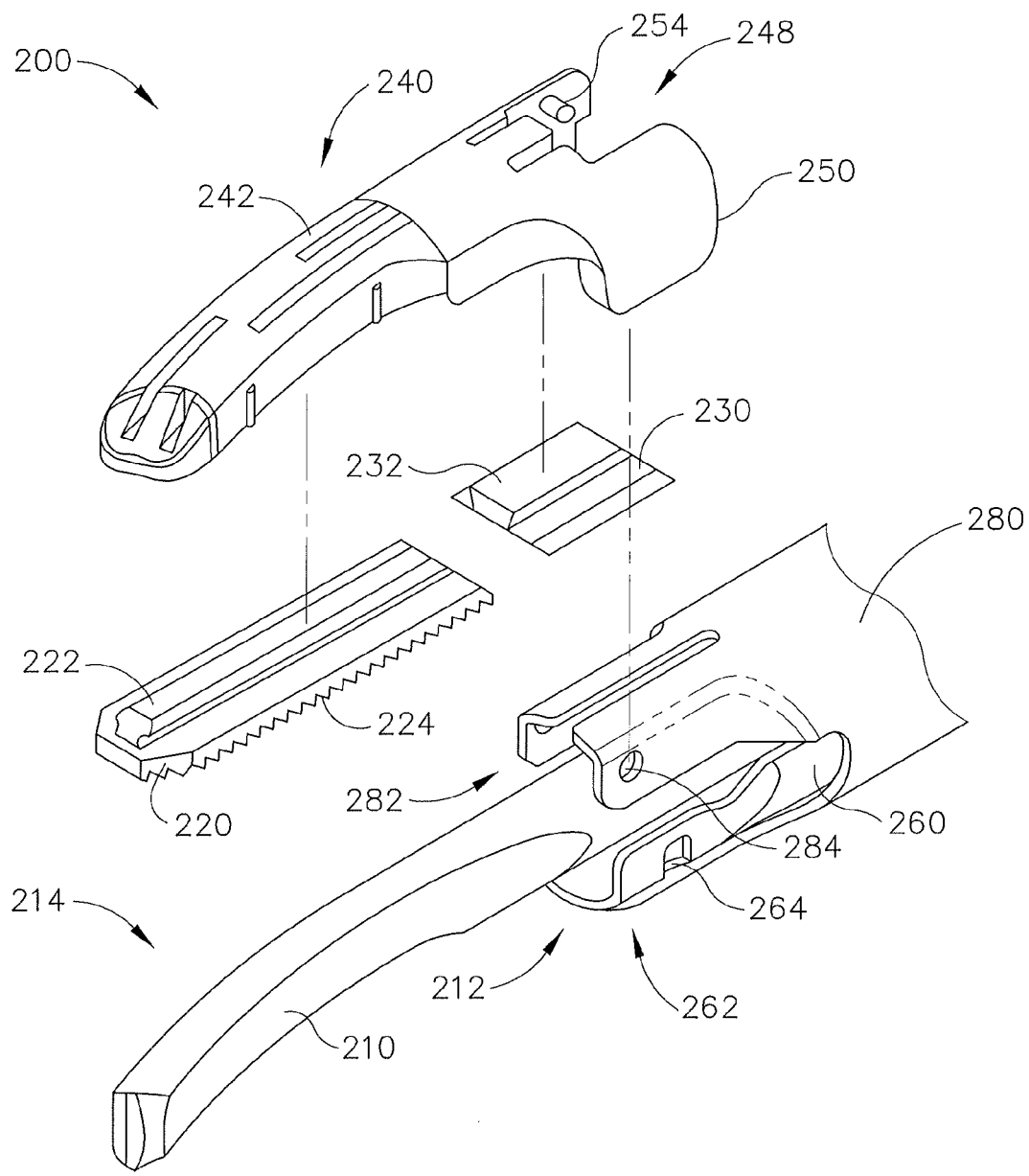
FIG. 2A depicts an exploded perspective view of an exemplary end effector shown in a closed position.
Figure 2B:
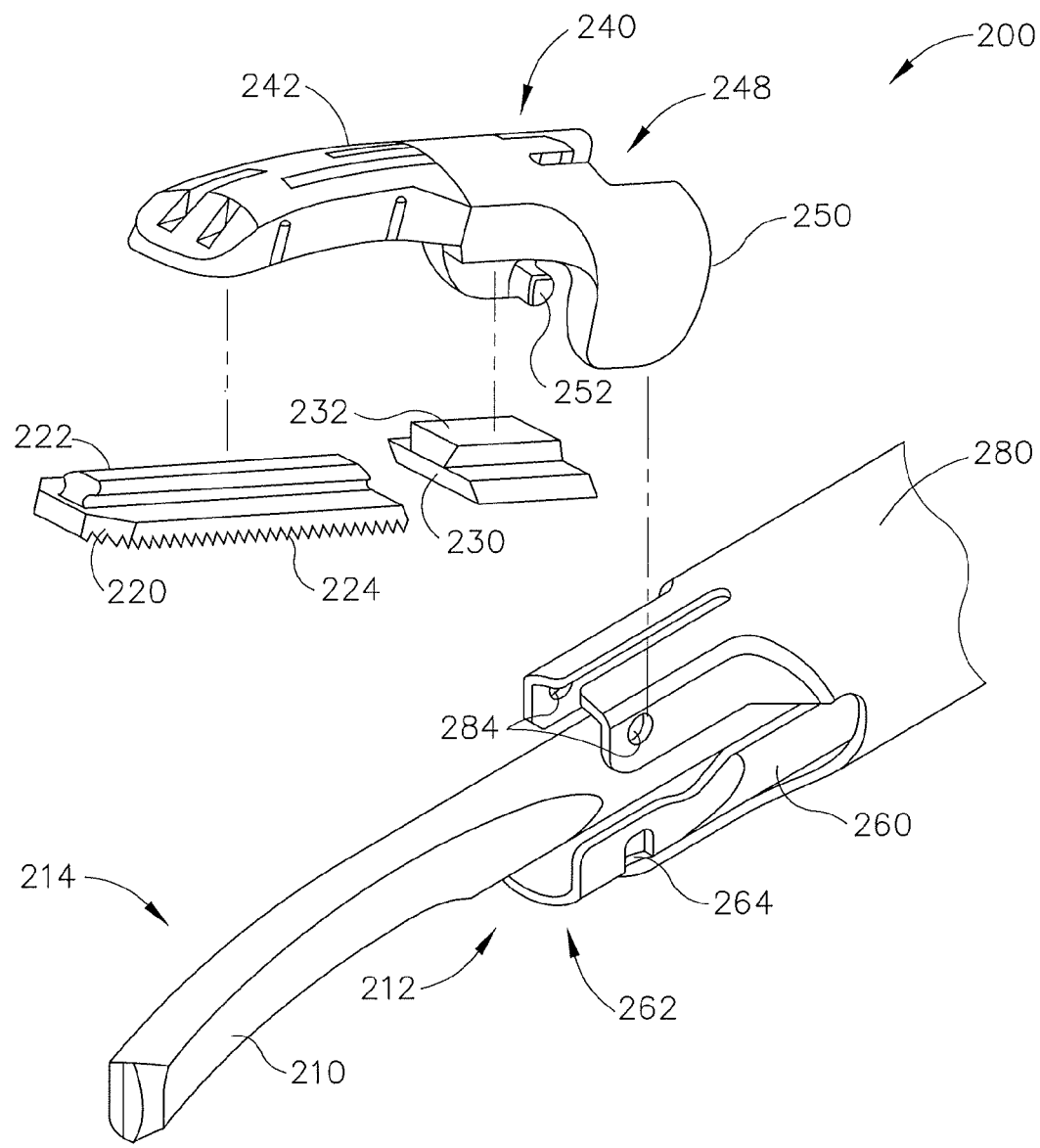
FIG. 2B depicts an exploded perspective view of the end effector of FIG. 2A shown in an open position.

FIGS. 2A-2B depict an exploded view of an exemplary end effector (200) shown in a closed position, FIG. 2A, and an open position, FIG. 2B. In the present example, end effector (200) comprises a blade (210), a distal clamp pad (220), a proximal clamp pad (230), a clamp arm (240), an inner tubular actuation member (260), and an outer sheath (280). Blade (210) may be constructed in accordance with at least some of the teachings of blade (82) described above or in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued Jun. 11, 2013 as U.S. Pat. No. 8,461,744; and/or U.S. Pat. Pub. No. 2009/0143797, issued Apr. 16, 2013 as U.S. Pat. No. 8,419,757, the disclosures of each are incorporated by reference herein. In the present example, blade (210) is configured to be coupled to a transducer, such as transducer (100), and to oscillate at an ultrasonic frequency. Such a coupling of blade (210) to the transducer may be via a waveguide (not shown). When tissue is secured between blade (210) and clamp arm (240), the ultrasonic oscillation of blade (210) may simultaneously sever tissue and denature the proteins in adjacent tissue cells, thereby providing a coagulative effect with relatively little thermal spread. An electrical current may also be provided through blade (210) and clamp arm (240) to cauterize the tissue. As shown, blade (210) comprises a cylindrical body portion (212) and a curved portion (214) at the distal end of blade (210). By way of example only, blade (210) comprises a solid titanium rod having a curved rectangular cuboid end. It should be understood that blade (210) may be substantially straight and/or blade (210) may have other geometries, including a conical end, a triangular prism end, a cylindrical end, a substantially planar end, a rectangular cuboid body, and/or any other geometry as will be apparent to one of ordinary skill in the art in view of the teachings herein. Further still, blade (210) may comprise materials other than titanium, including aluminium, steel, iron, composites, alloys, etc. Of course other configurations for blade (210) will be apparent to one of ordinary skill in the art in view of the teachings herein.

Distal clamp pad (220) of the present example comprises Teflon® (of E. I. du Pont de Nemours and Company of Wilmington, Del.). For instance, distal clamp pad (220) may be formed of steel that is coated with Teflon®. Alternatively, distal clamp pad (220) may be formed of any other suitable material and/or may be coated with any other suitable low low-friction materials, as will be apparent to one of ordinary skill in the art in view of the teachings herein. Distal clamp pad (220) mounts on to clamp arm (240) via a T-shaped member (222) extending from distal clamp pad (220) and insertable into a T-shaped recess (not shown) of clamp arm (240). Distal clamp pad (220) is pivotable to a position that is substantially parallel to, and in contact with, blade (210). Accordingly, when clamp arm (240) is actuated to the closed position, shown in FIG. 2A, tissue is compressed and grasped between distal clamp pad (220) and blade (210). As illustrated, distal clamp pad (220) includes a non-smooth surface (224), such as a saw tooth-like configuration, to enhance the gripping of tissue by distal clamp pad (220). The saw tooth-like configuration, or teeth, provide traction against the movement of tissue relative to blade (210). As will be appreciated by one of ordinary skill in the art, the saw tooth-like configuration is just one example of many tissue engaging surfaces that may be used to prevent movement of the tissue relative to the movement of blade (210). Other illustrative examples include bumps, interlaced patterns, tread patterns, a bead or sand blasted surface, etc. In the example shown, distal clamp pad (220) is insertable into clamp arm (240) at a distal end and is disposed distally of proximal clamp pad (230).

Proximal clamp pad (230) comprises a substantially flat clamp pad that includes Teflon® (of E. I. du Pont de Nemours and Company of Wilmington, Del.). For instance, proximal clamp pad (230) may be formed of steel that is coated with Teflon®. Alternatively, proximal clamp pad (230) may be formed of any other suitable material and/or may be coated with any other suitable low low-friction materials, as will be apparent to one of ordinary skill in the art in view of the teachings herein. Proximal clamp pad (230) mounts on to clamp arm (240) via a dove-tailed member (232) extending from proximal clamp pad (230) and insertable into a dove-tailed recess (not shown) of clamp arm (240). Proximal clamp pad (230) is also pivotable to a position that is substantially parallel to, and in contact with, blade (210). Accordingly, when clamp arm (240) is actuated to the closed position, shown in FIG. 2A, tissue is compressed between proximal clamp pad (230) and blade (210). Of course, since distal clamp pad (220) and proximal clamp pad (230) are distinct components, the material for distal clamp pad (220) and proximal clamp pad (230) may be different. Distal clamp pad (220) and proximal clamp pad (230) may be further constructed in accordance with at least some of the teachings of U.S. Pat. Pub. No. 2006/0079874, entitled "Tissue Pad for Use with an Ultrasonic Surgical Instrument," published Apr. 13, 2006, the disclosure of which is incorporated by reference herein.

Inner tubular actuation member (260) of the present example comprises a hollow cylindrical member configured to actuate longitudinally within outer sheath (280) while blade (210) extends longitudinally through inner tubular actuation member (260). The proximal end of inner tubular actuation member (260) is coupled to a trigger, such as trigger (68), configured to actuate inner tubular actuation member (260) proximally when the trigger is depressed. When the trigger is released, inner tubular actuation member (260) actuates distally. Distal end (262) of inner tubular actuation member (260) comprises a pair of actuation holes (264) disposed on opposing sides of inner tubular actuation member (260) and configured to receive a pair of lower pins (252) of clamp arm (240). Accordingly, when clamp arm (240) is coupled to inner tubular actuation member (260) via actuation holes (264) and lower pins (252), the longitudinal motion of inner tubular actuation member (260) pivots clamp arm (240) about a pair of upper pins (254) of clamp arm (240). Of course other configurations and coupling mechanisms for inner tubular actuation member (260) will be apparent to one of ordinary skill in the art in view of the teachings herein. For instance, inner tubular actuation member (260) may include living hinges and be constructed in accordance with at least some of the teachings of U.S. patent application Ser. No. 13/274,830, entitled "Surgical Instrument with Modular Clamp Pad," filed on even date herewith, published on May 10, 2012 as U.S. Pat. Pub. No. 2012/0116433, the disclosure of which is incorporated by reference herein. In some versions, inner tubular actuation member (260) may be omitted and a rod (not shown) may be coupled to clamp arm (240). The rod may thus be operable to pivot clamp arm (240).

Outer sheath (280) of the present example is also a hollow cylindrical member configured to couple to a casing of a handle assembly at a proximal end (not shown) of outer sheath (280) while blade (210), inner tubular actuation member (260), and the waveguide associated with blade (210) extend longitudinally therethrough. Outer sheath (280) has a distal end (282) that includes a pair of upper holes (284) disposed on opposing sides of outer sheath (280) and configured to receive a pair of upper pins (254) of clamp arm (240). As will be apparent to one of ordinary skill in the art, upper holes (284) provide a pivot point about which clamp arm (240) is pivotable. Outer sheath (280) is further configured to be longitudinally fixed relative to inner tubular actuation member (260). Thus, when inner tubular actuation member (260) actuates longitudinally, outer sheath (280) provides a mechanical ground enabling clamp arm (240) to be pivoted. Of course, outer sheath (280) need not necessarily be fixed relative to inner tubular actuation member (260). By way of example only, inner tubular actuation member (260) may be fixed and outer sheath (280) may be actuatable or, in other versions, both inner tubular member (260) and outer sheath (280) may be actuatable. Of course other configurations for outer sheath (280) will be apparent to one of ordinary skill in the art in view of the teachings herein. For instance, outer sheath (280) may include living hinges and be constructed in accordance with at least some of the teachings of U.S. Patent Application Ser. No. 13/274,830, entitled "Surgical Instrument with Modular Clamp Pad," filed on even date herewith, published on May 10, 2012 as U.S. Pat. Pub. No. 2012/0116433, the disclosure of which is incorporated by reference herein.

Clamp arm (240) comprises an engagement portion (242) and an attachment portion (248) proximal of engagement portion (242). Engagement portion (242) of the present example comprises a curved member having a substantially flat bottom face that includes a T-shaped recess configured to receive T-shaped member (222) of distal clamp pad (220). Engagement portion (242) has a curvature that is substantially similar to that of blade (210) of the present example. Of course if blade (210) is straight, then engagement portion (242) may also be straight. Engagement portion (242) may further be configured to curve downwardly about the sides of blade (210) such that engagement portion (242) forms a trough into which tissue may be compressed and severed by blade (210). Attachment portion (248) comprises a body member (250), a pair of lower pins (252), and a pair of upper pins (254). Body member (250) comprises a dove-tailed recess (not shown) configured to receive dove-tailed member (232) of proximal clamp pad (230). As discussed above, lower pins (252) are insertable into actuation holes (264) of inner tubular actuation member (260) and upper pins (254) are insertable into upper holes (284) of outer sheath (280). Accordingly, when pins (252, 254) are inserted into holes (264, 284), clamp arm (240) is coupled to outer sheath (280) and inner tubular actuation member (260), and clamp arm (240) is pivotable relative to blade (210). Of course other configurations for clamp arm (240) will be apparent to one of ordinary skill in the art in view of the teachings herein. In some versions, pins (252, 254) may be separate pins insertable through holes formed in body member (250). In some other versions, clamp arm (240) may include living hinges and be constructed in accordance with at least some of the teachings of U.S. patent application Ser. No. 13/274,930, entitled "Surgical Instrument with Modular Clamp Pad," filed on even date herewith, published on May 10, 2012 as U.S. Pat. No. 2012/0116433, the disclosure of which is incorporated by reference herein.

While one merely exemplary end effector (200) has been described herein, other end effectors may be used as well. For instance, clamp arm (240), distal clamp pad (220), proximal clamp pad (230), inner tubular actuation member (260), and/or outer sheath (280) may be omitted from end effector (200). One merely exemplary end effector omitting proximal clamp pad (230), inner tubular actuation member (260), and outer sheath (280) is described in U.S. Pat. Pub. No. 2007/0191713, entitled "Ultrasonic Device for Cutting and Coagulating," published Aug. 16, 2007, the disclosure of which is herein incorporated by reference. Another merely exemplary end effector omitting clamp arm (240), distal clamp pad (220), proximal clamp pad (230), and inner tubular actuation member (260) is described in U.S. Pat. Pub. No. 2008/0200940, entitled "Ultrasonic Device for Cutting and Coagulating," published Aug. 21, 2008, the disclosure of which is herein incorporated by reference. Still other configurations for end effector (200) will be apparent to one of ordinary skill in the art in view of the teachings herein.

B. Exemplary Threaded End Effector

FIG. 3 depicts a proximal end of an exemplary end effector (300) coupleable to a transmission assembly (350) via a threaded coupling. Transmission assembly (350) of the present example is coupled to a handle assembly (not shown) and includes a proximal outer sheath (360), a proximal tubular actuation member (370), and a waveguide (380). Waveguide (380) of transmission assembly (350) is coupled to a transducer (not shown), such as transducer (100), and waveguide (380) is configured to oscillate at the ultrasonic frequency produced by the transducer. Proximal tubular actuation member (370) is coupled to a trigger (not shown), such as trigger (68), and is configured to actuate longitudinally when the trigger is used. In some versions a force-limiting mechanism (not shown) may be coupled to proximal tubular actuation member (370) to reduce the actuating force when the trigger is at the end of its range of motion. Proximal outer sheath (360) is fixedly coupled to a handle assembly (not shown). In some versions proximal outer sheath (360) may be fixedly coupled to a rotation knob, such that proximal outer sheath (360) is rotatable relative to the handle assembly. Transmission assembly (350) may be further constructed in accordance with at least some of the teachings of transmission assemblies (70) described herein; U.S. patent application Ser. No.13/274,830, entitled "Surgical Instrument with Modular Clamp Pad," filed on even date herewith; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660 (now U.S. Pat. No. 8,461,744); and/or U.S. Pat. Pub. No. 2009/0143797.

End effector (300) of the present example comprises an outer sheath (310), an inner tubular actuation member (320), and a blade (330). It should be understood that the components of end effector (300) shown in FIG. 3 are merely exemplary and additional components may be included for end effector (300). For instance, end effector (300) may be further constructed in accordance with at least some of the teachings of end effectors (80, 200, 400, 700) described herein; U.S. patent application Ser. No. 13/274,830, entitled "Surgical Instrument with Modular Clamp Pad," filed on even date herewith; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660 (now U.S. Pat. No. 8,461,744); and/or U.S. Pat. Pub. No. 2009/0143797. For instance, end effector (300) may include a curved blade, a clamp arm, clamp pads, and/or any other components as will be apparent to one of ordinary skill in the art in view of the teachings herein. Of course one or more of outer sheath (310), inner tubular actuation member (320), and/or blade (330) may also be omitted from end effector (300).

As shown in FIG. 3, outer sheath (310) includes threading (312) that threadably couples to complementary threading (362) of proximal outer sheath (360). Likewise, inner tubular actuation member (320) includes threading (322) that threadably couples to complementary threading (372) of proximal tubular actuation member (370). Blade (330) includes a recess (332) having threading (334) configured to threadably receive a distal end of waveguide (380) having complementary threading (382). Accordingly, outer sheath (310), inner tubular actuation member (320), and blade (330) are threadably attachable to proximal outer sheath (360), proximal tubular actuation member (370), and waveguide (380) to couple end effector (300) to transmission assembly (350). As a result of such coupling, the ultrasonic oscillations produced by the transducer coupled to waveguide (380) are transmitted to blade (330). In addition, the longitudinal actuation of proximal tubular actuation member (370) via the trigger also longitudinally actuates inner tubular actuation member (320). Furthermore, when proximal outer sheath (360) is coupled to outer sheath (310), outer sheath (310) of end effector (300) is also fixedly coupled to the handle assembly and/or rotation knob. Thus, a user can thread end effector (300) onto transmission assembly (350) to use end effector (300) with the handle assembly. The user may also unthread end effector (300) from transmission assembly (350) to disengage end effector (300) from transmission assembly (350). Accordingly, a user may selectively couple various end effectors (300) onto transmission assembly (350) while still maintaining the mechanical and acoustic connections to operate end effector (300). For instance, if end effector (300) wears out and/or is no longer sterilized, the user may detach end effector (300) from transmission assembly (350) and dispose of end effector (300) while reusing transmission assembly (350).

In some versions, end effector (300) and/or transmission assembly (350) may comprise thixomolded parts, metal-injection-molded parts, plastic parts, and/or other parts as will be apparent to one of ordinary skill in the art in view of the teachings herein. In some versions, outer sheath (310), inner tubular actuation member (320), proximal outer sheath (360), and/or proximal tubular actuation member (370) may further include a slip feature to permit outer sheaths (310, 360) and tubular actuation members (320, 370) to synchronize for threading. For instance, ratcheting teeth (390) are circumferentially disposed about an interior surface of outer sheath (310) and an exterior surface of inner tubular actuation member (320) such that ratcheting teeth (390) engage and selectively restrict rotation between the two components until a sufficient rotational force is applied to cause ratcheting teeth (390) to slip. By way of example only, if tubular actuation members (320, 370) have fully threadably engaged each other but outer sheaths (310, 360) have not, a user may continue to rotate end effector (300), thereby causing ratcheting teeth (390) to slip due to the rotational resistance from tubular actuation members (320, 370) being fully threadably engaged. This permits a use to continue to threadably engage outer sheaths (310, 360) together while not over-tightening tubular actuation members (320, 370). It should be noted that ratcheting teeth (390) do not affect the translation of outer sheaths (310, 360) relative to inner tubular actuation members (320, 370). Instead, ratcheting teeth (390) merely restrict the rotation of outer sheaths (310, 360) relative to inner tubular actuation members (320, 370) and vice-versa. Of course ratcheting teeth (390) may be included between an exterior surface of proximal tubular actuation member (370) and an interior surface of outer sheath (360), between an exterior surface of blade (330) and an interior surface of inner tubular actuation member (320), between an exterior surface of waveguide (380) and an interior surface of proximal tubular actuation member (370). In some versions that omit tubular actuation members (320, 370), ratcheting teeth (390) may be provided between blade (330) and outer sheath (310) and/or between waveguide (380) and proximal outer sheath (360). Still other slip features will be apparent to one of ordinary skill in the art in view of the teachings herein. For instance, clutch plates, selectively disengageable pawls and gears, or etc., may be included in end effector (300) and/or transmission assembly (350). Alternatively, slip features may simply be omitted.

Alternatively, removable pins (not shown) may be inserted through end effector (300) and/or transmission assembly (350) to rotatably fix outer sheath (310), inner tubular actuation member (320), and blade (330) relative to each other, and rotatably fix proximal outer sheath (360), proximal tubular actuation member (370), and waveguide (380) relative to each other, such that end effector (300) and transmission assembly (350) may be coupled via the complementary threadings (312, 322, 334, 362, 372, 382). Once end effector (300) and transmission assembly (350) are coupled together, the pins may be removed to permit rotation of outer sheaths (310, 360), tubular actuation members (320, 370), and/or blade (330) and waveguide (380) relative to the others. It should be understood that the pins need not necessarily be removeable. Of course still further configurations for end effector (300) and/or transmission assembly (350) will be apparent to one of ordinary skill in the art in view of the teachings herein. For instance, in some versions, inner tubular actuation member (320) may be omitted and a rod (not shown) may be provided to pivot the clamp arm.

C. Exemplary Ratcheting End Effector

FIG. 4 depicts a proximal end of an exemplary alternative end effector (400) coupleable to a transmission assembly (450) via ratcheting teeth (412, 422, 462, 472). Transmission assembly (450) of the present example is coupled to a handle assembly (not shown) and includes a proximal outer sheath (460), a proximal tubular actuation member (470), and a waveguide (480). Waveguide (480) of transmission assembly (450) is coupled to a transducer (not shown), such as transducer (100), and waveguide (480) is configured to oscillate at the ultrasonic frequency produced by the transducer. Proximal tubular actuation member (470) is coupled to a trigger (not shown), such as trigger (68), and is configured to actuate longitudinally when the trigger is used. In some versions a force-limiting mechanism (not shown) may be coupled to proximal tubular actuation member (470) to reduce the actuating force when the trigger is at the end of its range of motion. Proximal outer sheath (460) is fixedly coupled to a handle assembly (not shown). In some versions proximal outer sheath (460) may be fixedly coupled to a rotation knob, such that proximal outer sheath (460) is rotatable relative to the handle assembly. Transmission assembly (450) may be further constructed in accordance with at least some of the teachings of transmission assemblies (70, 350) described above; U.S. Patent Application Ser. No. 13/274,830, entitled "Surgical Instrument with Modular Clamp Pad," filed on even date herewith, published on May 10, 2012 as U.S. Pat. Pub. No. 2011/0116433; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued Jun. 11, 2013 as U.S. Pat. No. 8,461,744; and/or U.S. Pat. Pub. No. 2009/0143797, issued Apr. 16, 2013 as U.S. Pat. No. 8,419,757.

End effector (400) of the present example comprises an outer sheath (410), an inner tubular actuation member (420), and a blade (430). It should be understood that end effector (400) may include additional components not shown in FIG. 4. For instance, end effector (400) may be further constructed in accordance with at least some of the teachings of end effectors (80, 200, 300, 700) described herein; U.S. patent application Ser. No. 13/274,830, entitled "Surgical Instrument with Modular Clamp Pad," filed on even date herewith, published on May 10, 2012 as U.S. Pat. Pub. No. 2012/0116433; U.S. Pat. Pub. No.2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued Jun. 11, 2013 as U.S. Pat. No. 8,461,744; and/or U.S. Pat. Pub. No. 2009/0143797, issued Apr. 16, 2013 as U.S. Pat. No. 8,419,757. For instance, end effector (400) may include a curved blade, a clamp arm, clamp pads, and/or any other components as will be apparent to one of ordinary skill in the art in view of the teachings herein.

As shown in FIG. 4, outer sheath (410) includes ratcheting teeth (412) that couple to complementary ratcheting teeth (462) of proximal outer sheath (460). Likewise, inner tubular actuation member (420) includes ratcheting teeth (422) that couple to complementary ratcheting teeth (472) of proximal tubular actuation member (470). Blade (430) includes a recess (432) having threading (434) configured to threadably receive a distal end of waveguide (480) having complementary threading (482). Accordingly, when blade (430) is threadably coupled to waveguide (480) via threading (434, 482), ratcheting teeth (412, 422, 462, 472) engage and ratcheting outer sheaths (410, 460) and tubular actuation members (420, 470) together. Thus, end effector (400) of the present example is coupleable to transmission assembly (450). As a result of such coupling, the ultrasonic oscillations produced by the transducer coupled to waveguide (480) are transmitted to blade (430). In addition, the longitudinal actuation of proximal tubular actuation member (470) via the trigger also longitudinally actuates inner tubular actuation member (420) via the engagement of ratcheting teeth (422, 472). Furthermore, when proximal outer sheath (460) is coupled to outer sheath (410), outer sheath (410) of end effector (400) is also fixedly coupled to the handle assembly and/or rotation knob via ratcheting teeth (412, 462).

Thus, a user can thread and ratchet end effector (400) onto transmission assembly (450) to use end effector (400) with the handle assembly. To disengage end effector (400) from transmission assembly (450), the user may initially unthread blade (430) from waveguide (480) via threading (434, 482). When the user is unthreading blade (430) from waveguide (480), ratcheting teeth (412, 422, 462, 472) resist disengagement. In some versions, ratcheting teeth (412, 422) of end effector (400) may be formed via injection molded plastic while ratcheting teeth (462, 472) may be formed via metal injection molding. Such molded components may comprise two half members that can be coupled together to form the whole piece. When blade (430) is threadably disengaged from waveguide (480), ratcheting teeth (412, 422) deform to disengage outer sheath (410) and inner tubular actuation member (420) from proximal outer sheath (460) and proximal tubular actuation member (470). With the deformation of ratcheting teeth (412, 422), the user removes end effector (400) from transmission assembly (450). A new end effector (400) may then be coupled to transmission assembly (450) and used. Accordingly, a user may selectively couple various end effectors (400) onto transmission assembly (450) while still maintaining the mechanical and acoustic connections to operate end effector (400). For instance, if end effector (400) wears out and/or is no longer sterilized, the user may detach end effector (400) from transmission assembly (450) and dispose of end effector (400) while reusing transmission assembly (450). Additional, the deformation of ratcheting teeth (412, 422) may also provide visual and/or tactile feedback that end effector (400) has previously been used. In some other versions, ratcheting teeth (412, 422) may comprise ratcheting screw threads such that a user may disengage ratcheting teeth (412, 422) by unthreading ratcheting teeth (412, 422). Other suitable configurations for end effector (400) and/or transmission assembly (450) will be apparent to one of ordinary skill in the art in view of the teachings herein. For instance, in some versions, inner tubular actuation member (420) may be omitted and a rod (not shown) may be provided to pivot the clamp arm.

D. Exemplary Bayonet Pin and Slot End Effector

FIGS. 5-9C depict the components and assembly of a surgical device utilizing an exemplary bayonet pin and slot detachable end effector.

i. Exemplary Transducer and Blade Assembly

Figure 5:
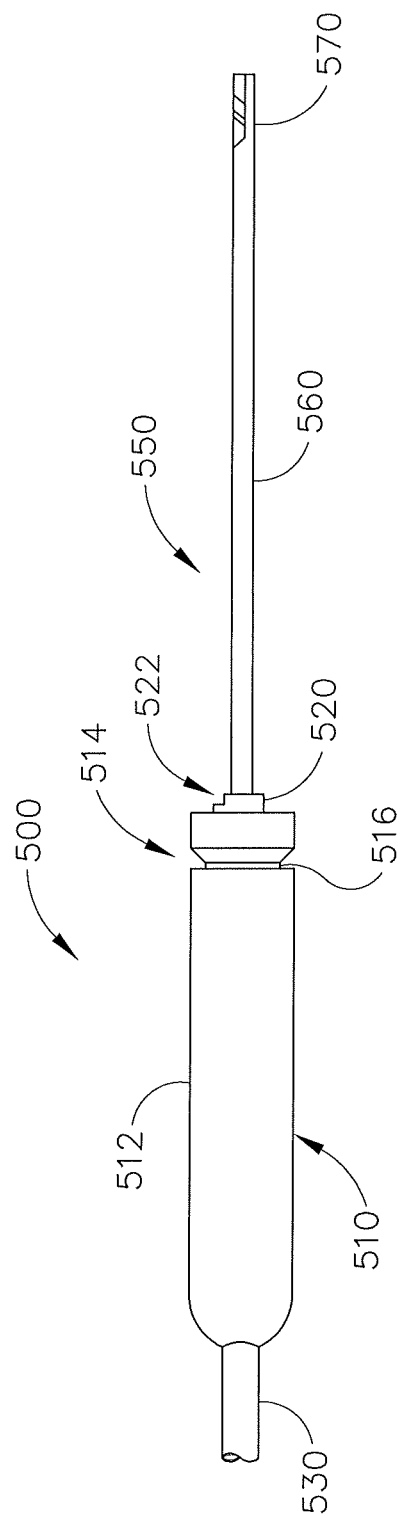
FIG. 5 depicts a side elevation view of an exemplary transducer and blade assembly.

FIG. 5 depicts a reusable transducer and blade assembly (500) for use in a handle assembly (600), shown in FIG. 6, with a detachable end effector (700), shown in FIG. 7. Transducer and blade assembly (500) comprises a transducer (510) and an elongated blade assembly (550) coupled to transducer (510) and extending distally from transducer (510). Transducer (510) of the present example comprises a transducer body (512), a circumferential notch (514) formed in a distal end of transducer body (512), a keyed slot member (520), and a cable (530). Cable (530) of the present example is coupleable to a power source, such as generator (20), to provide power to transducer (510). It should be understood that transducer (510) may be configured to omit cable (530), such as in a cordless transducer disclosed in U.S. Pat. Pub. No. 2009/0143797, issued Apr. 16, 2013as U.S. Pat. No. 8,419,757, entitled "Cordless Hand-held Ultrasonic Cautery Cutting Device," published Jun. 4, 2009, the disclosure of which is incorporated by reference herein.

Figure 9A:
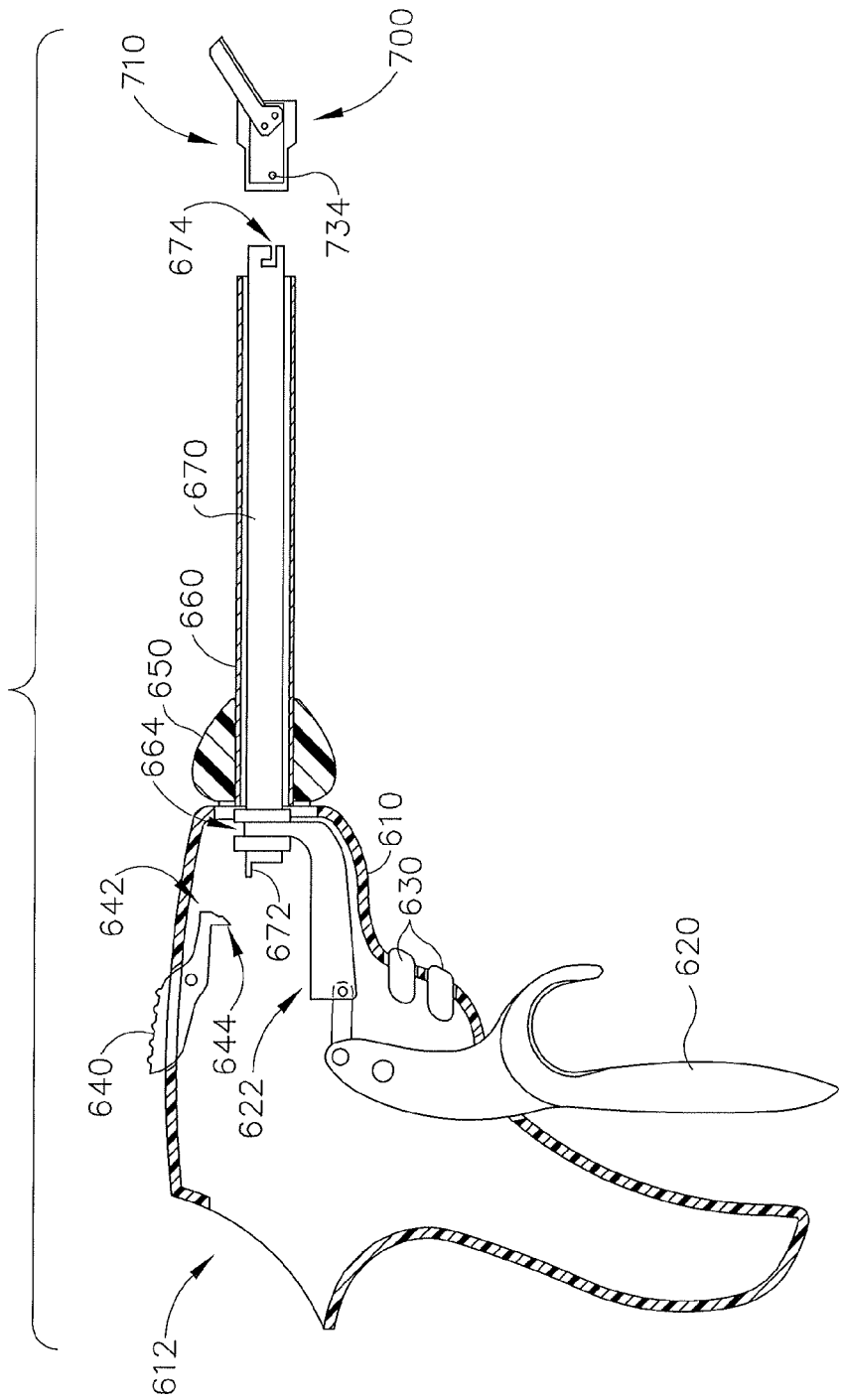
FIG. 9A depicts a side elevation view of the handle assembly of FIG. 6 and the end effector of FIG. 7 with a portion of the casing and outer sheath removed.
Figure 9B:
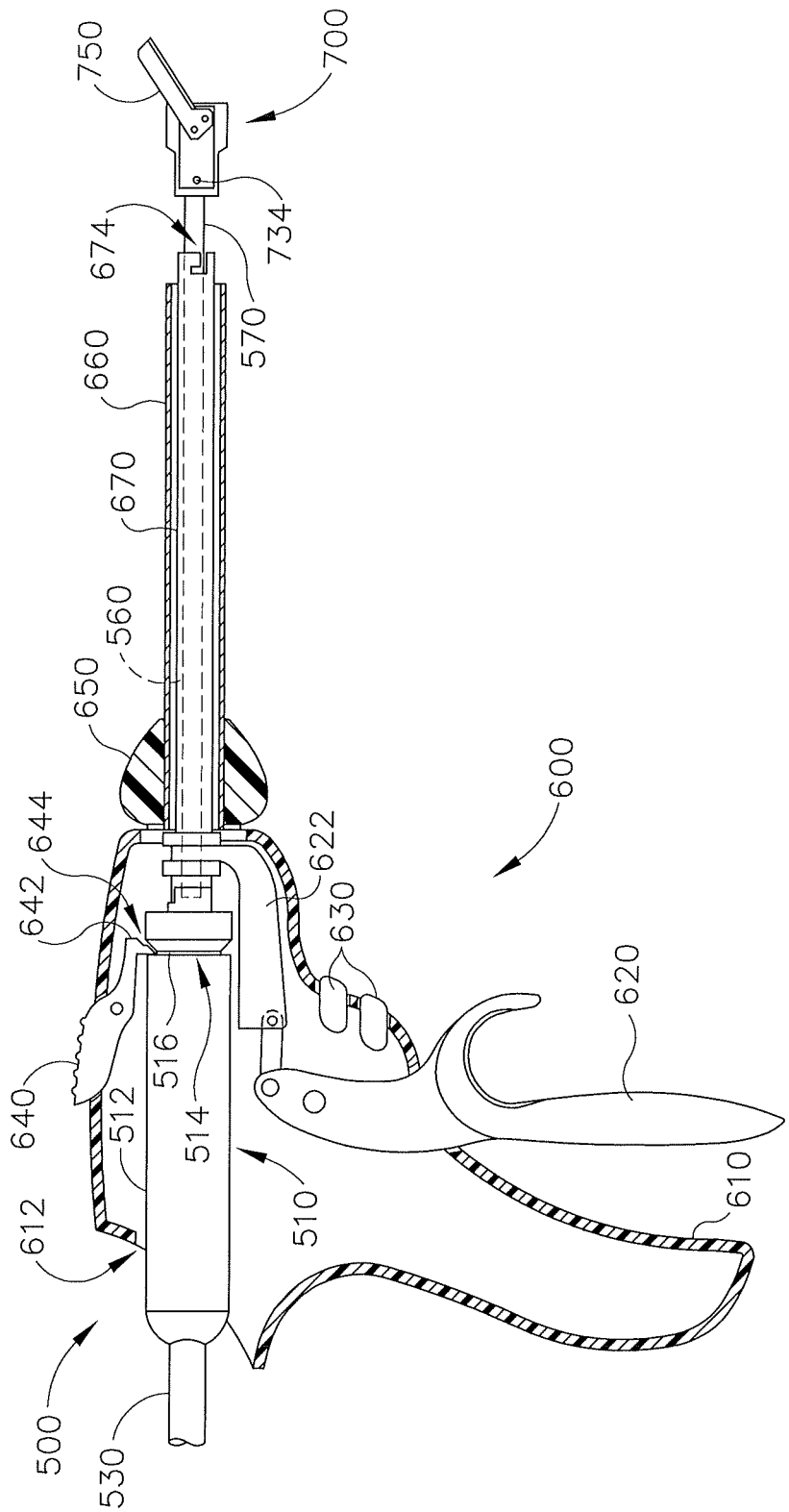
FIG. 9B depicts a side elevation view of the transducer and blade assembly of FIG. 5 inserted into the handle assembly of FIG. 9A.

Notch (514) comprises a circumferential groove in transducer body (512) configured to receive an end (642) of a latch member (640) to selectively latch transducer (510) into handle assembly (600), as will be discussed in more detail in reference to FIGS. 9A-9C. In some versions, notch (514) includes an electrical ring connector (516) that electrically couples to an electrical connector (644) on end (642) of latch member (640), shown in FIGS. 9A-9C, to electrically couple transducer (510) to components within handle assembly (600). For instance, such an electrical connection may couple transducer (510) to toggle buttons (630), shown in FIG. 6, or to an electrical switch (not shown) that activates transducer (510) when inserted into handle assembly (600). Of course other electrical connections may be provided to couple transducer (510) with electrical components of handle assembly (600).

Keyed slot member (520) comprises a cylindrical member having a longitudinal slot (522) configured to receive a key (672) on a proximal end of inner tubular actuation member (670), as will be discussed in more detail in reference to FIG. 8. Transducer (510) may further be constructed in accordance with at least some of the teachings of U.S. patent application Ser. No. 13/269,883, entitled "Surgical Instrument with Clutching Slip Ring Assembly to Power Ultrasonic Transducer," filed Oct. 10, 2011, published on Apr. 11, 2013 as U.S. Pat. Pub. No. 2013/0090675; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued Jun. 11, 2013 as U.S. Pat. No. 8,461,744; U.S. Pat. No. 6,500,176; U.S. Pat. Pub. No. 2011/0087218; and/or U.S. Pat. Pub. No. 2009/0143797, issued Apr. 16, 2013 as U.S. Pat. No. 8,419,757.

Blade assembly (550) comprises an elongated waveguide (560) and a distal blade (570). Waveguide (560) is coupled at a proximal end to transducer (510). In the present example waveguide (560) is fixedly coupled to transducer (510), though it should be understood that waveguide (560) may be detachable from transducer (510). Waveguide (560) oscillates at the ultrasonic frequency produced by transducer (510). In the present example, with distal blade (570) being coupled to waveguide (560), blade (570) also oscillates at the ultrasonic frequency. Thus, when tissue is secured between blade (570) and clamp arm (750) of end effector (700), described in more detail below, the ultrasonic oscillation of blade (570) may simultaneously sever tissue and denature the proteins in adjacent tissue cells, thereby providing a coagulative effect with relatively little thermal spread. In the present example, blade (570) is a curved blade, though in other versions, blade (570) may be straight or have other geometric configurations. Of course other configurations for blade assembly (550) will be apparent to one of ordinary skill in the art in view of the teachings herein.

ii. Exemplary Handle Assembly

Referring now to FIG. 6, handle assembly (600) of the present example comprises a casing (610), a pivotable trigger (620), a pair of toggle buttons (630), a latch member (640), a rotation knob (650), an outer sheath (660), and an inner tubular actuation member (670). It should be understood that trigger (620), toggle buttons (630), latch member (640), rotation knob (650), outer sheath (660), and inner tubular actuation member (670) are merely optional and may be omitted in some versions. Furthermore, handle assembly (600) may be constructed in accordance with at least some of the teachings of multi-piece handle assembly (60) described above or in accordance with at least some of the teachings of U.S. patent application Ser. No. 13/274,830, entitled "Surgical Instrument with Modular Clamp Pad," filed on even date herewith, published on May 10, 2012 as U.S. Pat. Pub. No. 2012/0116433; U.S. patent application Ser. No. 13/274,507, entitled "Gear Driven Coupling Between Ultrasonic Transducer and Waveguide in Surgical Instrument," filed on Oct. 17, 2011, published on May 10, 2012 as U.S. Pat. Pub. No. 2012/0116263; U.S. Patent Application Ser. No. 13/274,496, entitled "Cam Driven Coupling Between Ultrasonic Transducer and Waveguide in Surgical Instrument," filed on Oct. 17, 2011, published on May 10, 2012 as U.S. Pat. Pub. No. 2012/0116262; U.S. Patent Application Ser. No. 13/269,870entitled "Surgical Instrument with Modular Shaft and End Effector," filed Oct. 10, 2011, published on May 10,2012 as U.S. Pat. Pub. No. 2012/0116388; U.S. Patent Application Ser. No. 13/269,899, entitled "Ultrasonic Surgical Instrument with Modular End Effector," filed Oct. 10, 2011, published on Apr. 11, 2013 as U.S. Pat. Pub No. 2013/0090577; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued Jun. 1, 2013 as U.S. Pat. No. 8,461,744; U.S. Pat. No. 6,500,176; U.S. Pat. Pub. No. 2011/0087218; and/or U.S. Pat. Pub. No. 2009/0143797, issued Apr. 16, 2013 as U.S. Pat. No. 8,419,757, the disclosures of which are herein incorporated by reference.

In the present example, casing (610) includes a proximal aperture (612) configured to receive transducer and blade assembly (500) of FIG. 5. Trigger (620) is pivotably coupled to casing (610) and is configured to pivot from an open position, as shown in FIG. 6, to a closed position. Trigger (620) is configured to actuate outer sheath (660) distally via an actuation assembly (622) when trigger (620) is in the closed position, as will be discussed in more detail in reference to FIGS. 9A-9C. Toggle buttons (630) comprise buttons operable to selectively activate transducer (510) at different operational levels using a power source. For instance, a first toggle button (630) may activate transducer (510) at a maximum energy level while a second toggle (630) button may activate transducer (510) at a minimum, non-zero energy level. Of course, toggle buttons (630) may be configured for energy levels other than a maximum and/or minimum energy level as will be apparent to one of ordinary skill in the art in view of the teachings herein. Moreover, only a single toggle button (630) may be provided or more than two toggle buttons (630) may be provided. Toggle buttons (630) of the present example are configured to electrically couple to transducer (510) via ring connector (516) and electrical connector (644) of latch member (640), shown in FIGS. 9A-9C. Of course multiple circumferential grooves and/or electrical connectors may be included on transducer (510) and/or latch member (640) to provide multiple electrical couplings between components within handle assembly (600) and transducer (510). By way of example only, a plurality of ring connectors (516) may be disposed within notch (514) to couple to a plurality of electrical connectors (644) on latch member (640). Accordingly, various electrical components may be included within handle assembly (600) to electrically couple to transducer (510), and, in some versions, to an external power source such as generator (20) described above. Merely exemplary electrical components may include toggle buttons (630), sensors within handle assembly (600), sensors within end effector (700), cauterizing components for end effector (700), and/or any other suitable electrical components as will be apparent to one of ordinary skill in the art in view of the teachings herein. Such electrical couplings may provide electrical continuity even as transducer (510) is rotated relative to casing (610).

Latch member (640) is pivotably mounted to casing (610) and includes an end (642) configured to selectively insert into notch (514) of transducer (510) to longitudinally retain transducer (510) within casing (610), as will be discussed in more detail below. As shown in FIGS. 9A-9C, latch member (640) includes an electrical connector (644) configured to electrically couple to ring connector (516) of transducer (510). Of course a plurality of electrical connectors (644) and/or a plurality of latch members (640) may be included to electrically couple to a plurality of ring connectors (516). In the present example, latch member (640) is rotationally spring-loaded relative to casing (610) such that latch member (640) is urged to rotate about a pivot point in a clockwise direction as shown in FIGS. 9A-9C. Of course latch member (640) is merely optional. In some versions, an insertable clip may be inserted through a slot in casing (610) to longitudinally secure transducer (510) relative to casing (610) and/or to electrically couple transducer (510) to components within casing (610). In other versions, set screws and/or pins may be inserted into recesses within transducer (510) to mechanically and/or electrically couple transducer (510) to handle assembly (600). Still further suitable coupling members to retain and/or electrically couple transducer (510) to handle assembly (600) will be apparent to one of ordinary skill in the art in view of the teachings herein.

Rotation knob (650) is rotatably coupled to a distal end of casing (610) and is coupled to outer sheath (660) and inner tubular actuation member (670) to rotate outer sheath (660) and inner tubular actuation member (670) relative to casing (610). In some versions, outer sheath (660) and inner tubular actuation member (670) are configured to selectively couple to rotation knob (650). Merely exemplary selectively coupleable configurations are disclosed within U.S. patent application Ser. No. 13/269,899, entitled "Ultrasonic Surgical Instrument with Modular End Effector," filed Oct. 10, 2011, published on Apr. 11, 2013 as U.S. Pat. Pub. No. 2013/0090577 and U.S. Patent Application Ser. No. 13/269,870, entitled "Surgical Instrument with Modular Shaft and End Effector," filed Oct. 10, 2011, published on May 10, 2012 as U.S. Pat. Pub. No. 2012/0116388. Of course in other versions outer sheath (660) and inner tubular actuation member (670) may be fixed to rotation knob (650).

Outer sheath (660) comprises an elongate tubular member coupled to actuation assembly (622) at a proximal end of outer sheath (660) and having a first L-shaped slot (662) at the distal end. In the example shown in FIGS. 9A-9C, outer sheath (660) includes a circumferential groove (664) into which a portion of actuation assembly (622) is insertable. Outer sheath (660) is configured to actuate distally via actuation assembly (622) when trigger (620) is pivoted to the closed position. L-shaped slot (662) comprises a longitudinal portion (666) having an opening at the distal end and a circumferential portion (668) proximal of the distal end of outer sheath (660). Circumferential portion (668) further includes a lock portion (669) into which a first bayonet pin (714) of end effector (700) is insertable (as will be discussed in greater detail below). In some versions, lock portion (669) comprises a snap feature to retain first bayonet pin (714) therein. In further versions a spring-loaded cam (not shown) may be included to retain first bayonet pin (714) within lock portion (669). Further still, in other versions, threads (not shown) may be included on a distal end of outer sheath (660) instead of L-shaped slot (662) to threadably couple to complementary threads on end effector (700). In yet another arrangement, first bayonet pin (714) may comprise a spring loaded bayonet pin configured to be depressed and inserted into a hole (not shown) formed in outer sheath (660). Still further configurations for outer sheath (660) will be apparent to one of ordinary skill in the art in view of the teachings herein.

Inner tubular actuation member (670) comprises an elongate tubular member disposed within outer sheath (660) and rotatable relative to casing (610). In the present example, inner tubular actuation member (670) is longitudinally fixed relative to outer sheath (660) such that a clamp arm (750) is pivoted about the distal end of inner tubular actuation member (670) when outer sheath (660) actuates distally, as will be discussed in more detail later herein. The distal end of inner tubular actuation member (670) comprises a second L-shaped slot (674) at the distal end. L-shaped slot (674) comprises a longitudinal portion (676) having an opening at the distal end and a circumferential portion (678) proximal of the distal end of inner tubular actuation member (670). Circumferential portion (678) further includes a lock portion (679) into which a second bayonet pin (734) of end effector (700) is insertable. In some versions, lock portion (679) comprises a snap feature to retain second bayonet pin (734) therein. In other versions a spring-loaded cam (not shown) may be included to retain second bayonet pin (734) within lock portion (679). Further still, in other versions, threads (not shown) may be included on a distal end of inner tubular actuation member (670) instead of L-shaped slot (674) to threadably couple to complementary threads on end effector (700). In yet another arrangement, second bayonet pin (734) may comprise a spring loaded bayonet pin configured to be depressed and inserted into a hole (not shown) formed in inner tubular actuation member (670).

Referring now to FIG. 8, inner tubular actuation member (670) comprises a key (672) extending proximally from a proximal end of inner tubular actuation member (670) and configured to insert into slot (522) to rotationally align inner tubular actuation member (670) with transducer (510). In some versions, key (672) may be provided on waveguide (560) and/or blade (570) to align inner tubular actuation member (670) with waveguide (560) and/or blade (570). Still further configurations for inner tubular actuation member (670) and or alignment features to ensure alignment of end effector (700) with blade (570) will be apparent to one of ordinary skill in the art in view of the teachings herein.

iii. Exemplary End Effector

FIG. 7 depicts an exemplary end effector (700) configured to couple to outer sheath (660) and inner tubular actuation member (670) of handle assembly (600) of FIG. 6. End effector (700) of the present example comprises an outer sheath portion (710), an inner tube portion (730) (shown in phantom), and a clamp arm (750). Outer sheath portion (710) comprises an insertable portion (712) and an end portion (720), though it should be understood that end portion (720) is merely optional. For instance, end portion (720) may be omitted and insertable portion (712) may extend distally to the distal end of end effector (700). Insertable portion (712) comprises a tubular member configured to insert into the distal end of outer sheath (660). Insertable portion (712) further includes a first bayonet pin (714) extending outward from insertable portion (712) and configured to enter L-shaped slot (662) of outer sheath (660). End portion (720) of the present example is also a tubular member, but has an exterior diameter that is substantially equal to an exterior diameter of outer sheath (660). End portion (720) is connected to insertable portion (712) by a flared portion. End portion (720) comprises a first pivot pin (722) and a slot (724).

First pivot pin (722) is configured to pivotably couple a proximal end of clamp arm (750) to outer sheath portion (710). In some versions first pivot pin (722) is integrally formed on outer sheath portion (710). In other versions, first pivot pin (722) is integrally formed on clamp arm (750) and is insertable into a hole (not shown) in outer sheath portion (710). In still other versions, first pivot pin (722) is a separate pin that is insertable through holes in clamp arm (750) and outer sheath portion (710) and is attached to clamp arm (750) or outer sheath portion (710), such as by welding, adhesives, mechanical attachments, etc. Slot (724) is a longitudinal slot formed in a portion of outer sheath portion (710) and is configured to permit a second pivot pin (738) to slide within slot (724). Accordingly, when outer sheath portion (710) is coupled to outer sheath (660), and outer sheath (660) is actuated distally, second pivot pin (738) slides proximally within slot (724), thereby permitting clamp arm (750) to pivot about second pivot pin (738). Of course other configurations for outer sheath portion (710) will be apparent to one of ordinary skill in the art in view of the teachings herein.

Inner tube portion (730) (shown in phantom) comprises a tubular member configured to insert into the distal end of inner tubular actuation member (670). Inner tube portion (730) includes a second bayonet pin (734) (shown in phantom) extending outward from inner tube portion (730) and configured to enter second L-shaped slot (674) of inner tubular actuation member (670). Inner tube portion (730) further comprises a second pivot pin (738). Second pivot pin (738) is configured to pivotably couple a proximal end of clamp arm (750) to inner tube portion (730) through slot (724) of outer sheath portion (710). In some versions second pivot pin (738) is integrally formed on inner tube portion (730). In other versions, second pivot pin (738) is integrally formed on clamp arm (750) and is insertable into a hole (not shown) in inner tube portion (730). In still other versions, second pivot pin (738) is a separate pin that is insertable through holes in clamp arm (750) and inner tube portion (730) and is attached to clamp arm (750) or inner tube portion (730), such as by welding, adhesives, mechanical attachments, etc. Accordingly, when inner tube portion (730) is coupled to inner tubular actuation member (670), and outer sheath (660) is actuated distally, second pivot pin (738) slides proximally within slot (724), thereby permitting clamp arm (750) to pivot about second pivot pin (738). Of course other configurations for inner tube portion (730) will be apparent to one of ordinary skill in the art in view of the teachings herein. In some versions, inner tube portion (730) may be omitted and a rod (not shown) may be coupled to clamp arm (750) where second pivot pin (738) is indicated. The rod may be operable to pivot clamp arm (750) about first pivot pin (722). In such a configuration, a proximal end of the rod may be bent to form second bayonet pin (734). Of course the foregoing alternative is merely exemplary.

Clamp arm (750) comprises a proximal end pivotably coupled to inner tube portion (730) and outer sheath portion (710) such that clamp arm (750) is pivotable about a second pivot pin (738) described above. Clamp arm (750) of the present example also comprises a curved arm that is configured to compress tissue against blade (570) when clamp arm (750) is pivoted via trigger (620) described above. The curved arm of clamp arm (750) may be constructed in accordance with at least some of the teachings of clamp arm (240) described above. Clamp arm (750) further comprises a clamp pad (752), though it should be understood that this is merely optional. Clamp pad (752) may be constructed in accordance with at least some of the teachings of U.S. Pat. Pub. No. 2006/0079874, entitled "Tissue Pad for Use with an Ultrasonic Surgical Instrument," published Apr. 13, 2006, the disclosure of which is incorporated by reference herein. In some versions, clamp arm (750) may comprise a straight arm or may be omitted entirely.

Still further configurations for end effector (700) will be apparent to one of ordinary skill in the art in view of the teachings herein. For instance, end effector (700) may be constructed in accordance with at least some of the teachings of end effectors (80, 200, 300) described above; U.S. patent application Ser. No. 13/274,830, entitled "Surgical Instrument with Modular Clamp Pad," filed on even date herewith, published on May 10, 2012 as U.S. Pat. Pub. No. 2012/0116433; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued Jun. 11, 2013 as U.S. Pat. No. 8,461,744; U.S. Pat. Pub. No. 2009/0143797, issued Apr. 16, 2013 as U.S. Pat. No. 8,419,757.

iv. Exemplary Assembly of a Surgical Instrument Having an Exemplary Bayonet Pin and Slot End Effector FIGS. 9A-9C depict the assembly of a surgical instrument having transducer and blade assembly (500) of FIG. 4, handle assembly (600) of FIG. 5, and end effector (700) of FIG. 7. FIG. 9A shows casing (610) with a proximal aperture (612) configured to receive transducer and blade assembly (500). End effector (700) is shown aligned with outer sheath (660) and inner tubular actuation member (670), but in a detached position. Initially the user inserts transducer and blade assembly (500) through proximal aperture (612). Blade assembly (550) is guided through inner tubular actuation member (670) and out through the distal end of inner tubular actuation member (670), as shown in FIG. 9B. When transducer and blade assembly (500) is fully inserted, latch member (640) engages notch (514) to retain transducer and blade assembly (500) longitudinally within handle assembly (600). Latch member (640) may be spring-loaded to automatically engage notch (514), or latch member (640) may be manually rotated to engage notch (514). In the example shown in FIG. 9B, when end (642) engages notch (514), electrical connector (644) electrically couples to ring connector (516) within notch (514). It should be understood that transducer and blade assembly (500) can freely rotate relative to handle assembly (600) while still maintaining an electrical connection between electrical connector (644) and ring connector (516). In addition, as transducer and blade assembly (500) is inserted into handle assembly (600), a user may rotate transducer and blade assembly (500) and/or inner tubular actuation member (670) to align key (672) with slot (522). Such an alignment maintains the orientation between blade (570) and clamp arm (750) of end effector (700). For instance, in the present example, blade (570) and clamp arm (750) are both curved members, and misalignment of blade (570) to clamp arm (750) may reduce the efficacy of the surgical instrument and/or prevent end effector (700) from adequately clamping down onto tissue. In addition or in the alternative, key (672) may be provided on the proximal end of end effector (700) and slot (522) may be provided on a distal end of inner tubular actuation member (670) or vice versa.

Figure 9C:
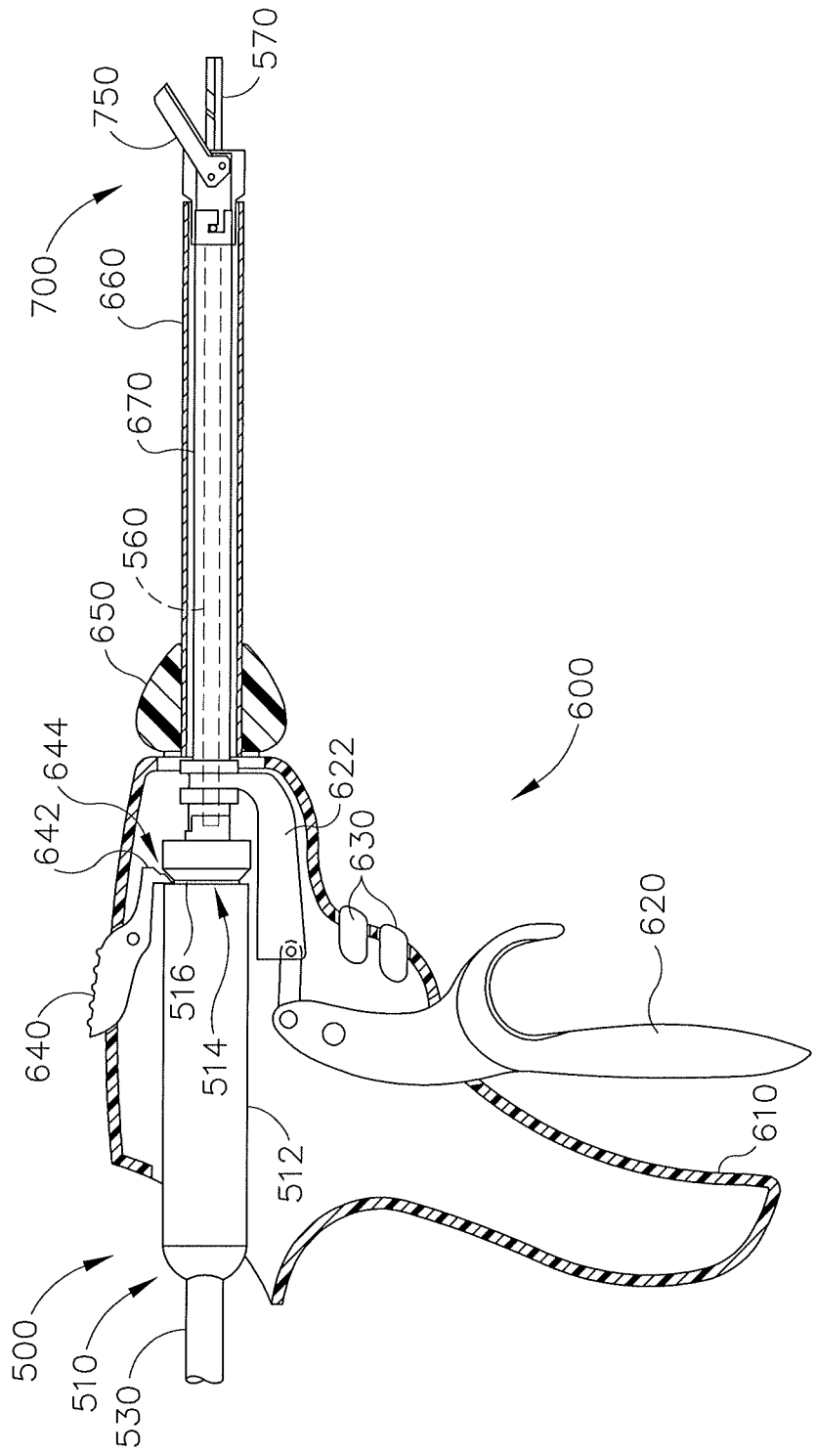
FIG. 9C depicts a side elevation view of the end effector of FIG. 7 coupled to the handle assembly of FIG. 9A with the transducer and blade assembly extending therethrough.

With transducer and blade assembly (500) axially restrained within handle assembly (600), end effector (700) of the present example is then attached to outer sheath (660) and inner tubular actuation member (670) as shown in FIG. 9C. It should be understood that in some versions end effector (700) is coupled to outer sheath (660) and inner tubular actuation member (670) prior to the coupling of transducer and blade assembly (500). In the present example, L-shaped slots (662, 674) of inner tubular actuation member (670) and outer sheath (660) are aligned such that bayonet pins (714, 734) are insertable into longitudinal portions (666, 676) of each L-shaped slot (662, 674). When bayonet pins (714, 734) reach the proximal end of longitudinal portions (666, 676), the user rotates end effector (700) to rotate bayonet pins (714, 734) into radial portions (668, 678) until bayonet pins reach lock portions (669, 679). In some versions a retention feature, such as a snap feature, a spring-loaded cam, or etc., may be used to further secure bayonet pins (714, 734) within L-shaped slots (662, 674). With end effector (700) and transducer and blade assembly (500) coupled to handle assembly (600), the user may then use the surgical instrument for a procedure.

In the present example, trigger (620) is pivotable to a closed position to actuate actuation assembly (622) and outer sheath (660) distally. In this example, inner tubular actuation member (670) is axially fixed relative to the actuation of outer sheath (660). Accordingly, outer sheath (660) actuates first pivot pin (722) distally to rotate clamp arm (750) into a closed position, thereby clamping tissue between clamp arm (750) and blade (570). In some versions, actuation assembly (622) may actuate outer sheath (660) proximally. In other versions, actuation assembly (622) may be coupled to inner tubular actuation member (670) to actuate inner tubular actuation member (670) proximally or distally while outer sheath (660) is fixed relative to the actuation of inner tubular actuation member (670). Transducer (510) may then be activated (if it already is not active) to oscillate blade (570) to simultaneously sever tissue and denature the proteins in adjacent tissue cells, thereby providing a coagulative effect with relatively little thermal spread. Accordingly, a user may use the assembled surgical device to sever and coagulate tissue during a surgical procedure. When trigger (620) is pivoted to an open position, actuation assembly (622) actuates proximally and clamp arm (750) is opened.

When finished with the procedure, the user may decouple end effector (700) and transducer and blade assembly (500) from handle assembly (600). For instance, the user may simply twist and pull on end effector (700) to disengage bayonet pins (714, 7340. In some versions including spring loaded bayonet pins (714, 734), a sleeve (not shown) may be provided on the outside of outer sheath (660), between outer sheath (660) and inner tubular actuation member (670), and/or inside of inner tubular actuation member (670) such that the sleeve may be translated distally to depress the spring loaded bayonet pins (714, 734). End effector (700) may then be removed. In some versions, the sleeve may be spring biased in the proximal direction.

End effector (700) of the present example comprises a disposable component that be discarded after a procedure. In some versions, end effector (700) may be cleaned and reused with transducer and blade assembly (500) and/or handle assembly (600). Transducer and blade assembly (500) comprise a reusable component that may be cleaned and/or reclaimed to be reused with handle assembly (600), end effector (700), and/or a new end effector (700). Of course, in some versions transducer and blade assembly (500) may be a disposable component as well, or if transducer (510) is decoupleable from blade assembly (550), transducer (510) may be reusable while blade assembly (550) is disposed of. In yet a further alternative, blade assembly (550) may be disassembled into blade (570) and waveguide (560) such that blade (570) may be disposed of while waveguide (560) and transducer (510) are cleaned and reused. Handle assembly (600) of the present example comprises a reusable component that may be cleaned and/or reclaimed to be reused with transducer and blade assembly (500), end effector (700), and/or a new end effector (700). Of course, in some versions handle assembly (600) may be a disposable component as well, or if outer sheath (660) and/or inner tubular actuation member (670) are decoupleable from the remainder of handle assembly (600), the remainder of handle assembly (600) may be reusable while outer sheath (660) and/or inner tubular actuation member (670) are disposed of.

Other configurations for transducer and blade assembly (500), handle assembly (600), and/or end effector (700) will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly comprising:
      i. a casing,
      ii. a first elongate member extending distally from the casing,
      iii. a second elongate member extending distally from the casing, wherein the second elongate member is operable to translate relative to the first elongate member, and
      iv. a transducer engagement feature movably coupled with the casing, wherein at least a portion of the transducer engagement feature extends from the casing, wherein the transducer engagement feature comprises an electrical connector; and
   (b) a transducer and blade assembly comprising:
      i. a transducer, wherein the transducer engagement feature is movable relative to the casing to selectively restrain the transducer within the casing, wherein the transducer comprises a notch having a ring connector disposed therein, and
      ii. a blade assembly acoustically coupled to and extending distally from the transducer, wherein the blade assembly is operable to sever tissue.

2. The surgical instrument of claim 1 wherein the transducer engagement feature is operable to axially restrain the transducer and blade assembly within the casing.

3. The surgical instrument of claim 1 wherein the body assembly comprises a trigger pivotably coupled to the casing and operable to actuate the second elongate member longitudinally relative to the casing.

4. The surgical instrument of claim 1 wherein the body assembly further comprises a slip feature disposed between the first and second elongate members, wherein the slip feature is operable to selectively permit the second elongate member to rotate relative to the first elongate member.

5. The surgical instrument of claim 1, wherein the transducer engagement feature comprises a latch.

6. The surgical instrument of claim 1, wherein the blade assembly is removably coupled with the transducer.

7. The surgical instrument of claim 1 further comprising a removable distal end assembly comprising:
   i. a first member configured to selectively couple with a distal portion of the first elongate member, and
   ii. a second member configured to selectively couple with a distal portion of the second elongate member.

8. The surgical instrument of claim 7 wherein the second member is insertable into the second elongate member.

9. The surgical instrument of claim 8 wherein the second member comprises a first bayonet pin, wherein the second elongate member comprises a first slot, and wherein the first bayonet pin and first slot form a bayonet connection.

10. The surgical instrument of claim 9 wherein the first slot comprises a retention feature to selectively retain the first bayonet pin therein 11. The surgical instrument of claim 9 wherein the first slot is an L-shaped slot.

12. The surgical instrument of claim 7 wherein the first elongate member comprises an inner tubular actuation member rotatable relative to the body assembly and disposed within the second elongate member.

13. The surgical instrument of claim 12 wherein the inner tubular actuation member comprises a key extending proximally from a proximal end of the inner tubular actuation member and wherein the transducer comprises a keyed member having a complementary longitudinal slot configured to receive the key.

14. The surgical instrument of claim 12, further comprising a clamp arm, wherein the clamp arm is operable to clamp tissue against a distal end of the blade assembly, wherein the second member is operable to selectively pivot the clamp arm relative to the first member upon translation of the second elongate member relative to the first elongate member, wherein the first member comprises an inner tube portion that is insertable into the inner tubular actuation member, wherein the clamp arm is pivotably coupled to the inner tube portion, wherein the inner tube portion comprises a second bayonet pin, wherein the inner tubular actuation member comprises a second slot, and wherein the second bayonet pin and second slot form a bayonet connection.

15. The surgical instrument of claim 14 wherein the second slot comprises a retention feature to selectively retain the second bayonet pin therein.

16. The surgical instrument of claim 14 wherein the clamp arm comprises a curved arm, wherein the blade assembly comprises a curved blade, wherein a key and longitudinal slot align the curved arm with the curved blade when the key is inserted into the longitudinal slot.

17. The surgical instrument of claim 7 wherein the removable distal end assembly is threadably coupleable to a distal end of the first elongate member.

18. A surgical instrument comprising:
 (a) a body assembly comprising:
  i. a casing,
  ii. a proximal outer sheath extending distally from the casing,
  iii. a proximal inner tubular member disposed within the proximal outer sheath,
  iv. a waveguide disposed within the proximal inner tubular member, and
  v. a slip feature; and
 (b) an end effector comprising:
  i. a distal outer sheath, wherein the distal outer sheath is selectively coupleable to the proximal outer sheath,
  ii. a distal inner tubular member disposed within the distal outer sheath, wherein the distal inner tubular member is selectively coupleable to the proximal inner tubular member, and
  iii. a blade disposed within the distal inner tubular member, wherein the blade is selectively coupleable to the waveguide;
 wherein the entire end effector is operable to be coupled or decoupled from the proximal outer sheath, the proximal inner tubular member, and the waveguide as an assembly, wherein the slip feature is configured to limit the force applied to the proximal inner tubular member when the end effector is coupled to the proximal outer sheath, the proximal inner tubular member, and the waveguide.

19. The surgical instrument of claim 18, wherein the slip feature is disposed between the proximal outer sheath and the proximal inner tubular member.

20. A surgical instrument comprising:
 (a) a body assembly comprising:
  i. a casing,
  ii. a shaft extending distally from the casing,
  iii. an ultrasonic transducer at least partially disposed within the casing, and
  iv. a pivoting member, wherein the pivoting member is pivotably coupled to the casing, wherein a first end of the pivoting member comprises an electrical connector, wherein a second end of the pivoting member extends from the casing, wherein the pivoting member is configured to selectively electrically connect with the ultrasonic transducer and to further selectively prevent longitudinal translation of the ultrasonic transducer relative to the casing; and
 (b) an acoustic transmission assembly configured to removably couple with the transducer.

* * * * *